(12) United States Patent  (10) Patent No.: US 9,101,712 B2
Denis et al.  (45) Date of Patent: Aug. 11, 2015

(54) OCCLUSION DETECTION METHOD

(75) Inventors: Scott A. Denis, Murrieta, CA (US);
Silke Williams, San Diego, CA (US)

(73) Assignee: ZEVEX, INC., Salt Lake City, UT (US)

( * ) Notice: Subject to any disclaimer, the term of this patent is extended or adjusted under 35 U.S.C. 154(b) by 643 days.

(21) Appl. No.: 13/416,302

(22) Filed: Mar. 9, 2012

(65) Prior Publication Data
US 2013/0238261 A1    Sep. 12, 2013

(51) Int. Cl.
G06F 19/00 (2011.01)
A61M 5/142 (2006.01)
A61M 5/168 (2006.01)

(52) U.S. Cl.
CPC ....... *A61M 5/16831* (2013.01); *A61M 5/16854* (2013.01); *G06F 19/3468* (2013.01); *A61M 2005/16863* (2013.01); *A61M 2005/16868* (2013.01); *A61M 2005/16872* (2013.01); *A61M 2205/12* (2013.01)

(58) Field of Classification Search
CPC .......... G06F 19/3468; A61M 5/16854; A61M 2005/16872; A61M 2005/16868; A61M 5/16831; A61M 2005/16863
USPC .............. 702/50; 604/65, 151, 153, 300, 500; 128/DIG. 13
See application file for complete search history.

(56) References Cited

U.S. PATENT DOCUMENTS

| 4,863,425 | A | | 9/1989 | Slate et al. | |
|---|---|---|---|---|---|
| 4,950,235 | A | * | 8/1990 | Slate et al. | 604/65 |
| 5,096,385 | A | * | 3/1992 | Georgi et al. | 417/18 |
| 5,103,211 | A | * | 4/1992 | Daoud et al. | 340/608 |
| 5,116,203 | A | | 5/1992 | Natwick et al. | |
| 5,356,378 | A | * | 10/1994 | Doan | 604/65 |
| 5,419,684 | A | * | 5/1995 | Struble et al. | 417/44.2 |
| 5,514,102 | A | | 5/1996 | Winterer et al. | |
| 5,522,799 | A | * | 6/1996 | Furukawa | 604/65 |
| 5,695,473 | A | * | 12/1997 | Olsen | 604/153 |
| 5,720,721 | A | | 2/1998 | Dumas et al. | |
| 5,791,881 | A | | 8/1998 | Moubayed et al. | |

(Continued)

FOREIGN PATENT DOCUMENTS

| WO | 9603168 | 2/1996 |
|---|---|---|
| WO | 2009143336 | 11/2009 |
| WO | 2013134448 | 9/2013 |

OTHER PUBLICATIONS

MHRA Evaluation Report No. 04008, Volumetric Pump, Arcomedical Volumed μVP7000 PVC, Apr. 2004.

(Continued)

*Primary Examiner* — Carol S Tsai
(74) *Attorney, Agent, or Firm* — Hodgson Russ LLP

(57) ABSTRACT

Methods for improving the accuracy of occlusion sensor baselines in an infusion pump are described. An infusion pump includes logic for making an antiratchet decision for determining whether a new administration set was installed after there has been access to the administration set. If so, then new occlusion sensor baselines are established. If not, then the current baselines are maintained. The antiratchet decision logic may depend upon the value of a baseline delta equal to a difference between the upstream sensor signal and the downstream sensor signal. In another aspect, an upstream occlusion sensor baseline is shifted in correspondence with decreases in the upstream sensor signal occurring while a pumping mechanism of the infusion pump is not operating to compensate for sensor signal drift.

13 Claims, 26 Drawing Sheets

(56) References Cited

U.S. PATENT DOCUMENTS

| | | | |
|---|---|---|---|
| 5,827,223 A | 10/1998 | Butterfield | |
| 5,935,106 A * | 8/1999 | Olsen | 604/153 |
| 6,077,055 A | 6/2000 | Vilks | |
| 6,241,704 B1 | 6/2001 | Peterson et al. | |
| 6,422,057 B1 * | 7/2002 | Anderson | 73/1.36 |
| 6,558,347 B1 * | 5/2003 | Jhuboo et al. | 604/67 |
| 6,572,604 B1 * | 6/2003 | Platt et al. | 604/500 |
| 6,648,861 B2 * | 11/2003 | Platt et al. | 604/300 |
| 7,880,624 B2 | 2/2011 | DelCastilio et al. | |
| 8,182,461 B2 * | 5/2012 | Pope et al. | 604/503 |
| 8,486,020 B2 * | 7/2013 | Hills et al. | 604/151 |
| 8,608,699 B2 * | 12/2013 | Blomquist | 604/151 |
| 8,752,436 B2 * | 6/2014 | Beck et al. | 73/756 |
| 2001/0031944 A1 * | 10/2001 | Peterson et al. | 604/65 |
| 2005/0096593 A1 | 5/2005 | Pope et al. | |
| 2010/0057058 A1 | 3/2010 | Ziegler et al. | |

OTHER PUBLICATIONS

CADD-Solis Ambulatory Infusion Pump Technical Manual, Smiths Medical, 2008.

Flo-Gard 6301 Dual Channel Volumetric Infusion Pump, Operator's Manual, Baxter, 1999.

* cited by examiner

*OcclusionInit*

*OcclusionReset*

*OcclusionReset*

*OcclusionPreMotorCheck*

*OcclusionPreMotorCheck*

*OcclusionCheck*

*OcclusionPostMotorCheck*

*DetectOcclusion*

*DetectOcclusion*

*DetectOcclusion*

*DetectOcclusion*

*DetectOcclusion*

*DetectOcclusion*

*DetectOcclusion*

*AntiRatchet*

*AntiRatchet*

*OccBaselineDelta*

*DownstreamOcclusionDetected*

*DownstreamOcclusionDetected*

*UpstreamOcclusionDetected*

*UpstreamOcclusionDetected*

*OcclusionPendingDownstream*

*OcclusionPendingUpstream*

OCCLUSION DETECTION METHOD

FIELD OF THE INVENTION

The present invention relates to the field of medical infusion pumps, and more particularly to methods of detecting an occlusion or blockage in tubing through which fluid is pumped.

BACKGROUND OF THE INVENTION

Programmable infusion pumps for delivering nutritional fluids and medicine to patients in accordance with predetermined fluid delivery parameters are in wide usage. One type of infusion pump is a peristaltic pump arranged along flexible connective tubing carrying fluid from a fluid source to the patient. The peristaltic pump has a pumping mechanism for progressively squeezing successive portions of the tubing to cause fluid to flow through the tubing in a flow direction toward the patient. In a common arrangement, the pumping mechanism includes a motor-driven wheel having radial fingers or rollers that engage a segment of the tubing arranged about a circumferential portion of the wheel. As the wheel rotates, fluid is pumped through the tubing to the patient. The tubing segment arranged about the pump wheel may be held in a U-shaped configuration by a cassette designed for receipt in a channel or receptacle area of the pump. The cassette may provide terminals for connecting an incoming line of tubing coming from the fluid source and an outgoing line of tubing going to the patient to opposite ends of the U-shaped tubing segment received by the pump. In the present specification, the terms "upstream" and "downstream" are in reference to the direction of fluid flow caused by the pumping mechanism. For example, the incoming line of tubing is "upstream" from the pumping mechanism, and the outgoing line of tubing is "downstream" from the pumping mechanism.

A recognized concern, especially when pumping viscous nutritional fluids for enteral feeding, is the formation of blockages ("occlusions") within the tubing that may reduce or completely prevent flow. As a safety measure, it is known to provide a pair of occlusion sensors on the infusion pump. An upstream occlusion sensor is arranged to engage the tubing at an upstream location relative to the pumping mechanism, and a downstream occlusion sensor is arranged to engage the tubing at a downstream location relative to the pumping mechanism. The occlusion sensors may include transducers or strain gauges that detect deflection of the flexible tubing wall caused by a local pressure differential (either pressure increase or decrease) relative to an equilibrium fluid pressure within the tubing and provide an electronic signal indicative of the deflection. For example, if an occlusion forms at a location in the downstream tubing between the pump and the patient, a bulge or outward deflection of the tubing wall will be detectable by the downstream occlusion sensor. Conversely, if an occlusion forms at a location in the upstream tubing between the fluid source and the pump, the continued operation of the pumping mechanism creates a vacuum between the occlusion location and the pumping mechanism and an inward deflection of the tubing wall will be detectable by the upstream occlusion sensor.

The signals from the upstream and downstream occlusion sensors are monitored and compared to respective signal baselines to detect occlusion. The upstream sensor signal baseline is the signal provided by the upstream sensor corresponding to a condition of fluid pressure equilibrium at the upstream sensor location. Likewise, the downstream sensor signal baseline is the signal provided by the downstream sensor corresponding to a condition of fluid pressure equilibrium at the downstream sensor location. The upstream and downstream baselines may be established by an initialization routine executed when the pump is started up. During pump operation for infusion, respective differences between the upstream sensor signal and upstream baseline, and between the downstream sensor signal and downstream baseline, are monitored. If a difference between the sensor signal and the corresponding baseline exceeds a predetermined threshold for a predetermined period of time, an upstream occlusion is detected. As will be understood, establishing and maintaining valid baselines for the upstream and downstream occlusion sensors is essential for proper occlusion detection.

One situation where an invalid baseline may inadvertently be used occurs when an occlusion is detected, pump operation is stopped, and a door of the pump is opened to access the cassette and tubing to permit replacement of the occluded tubing. If new tubing is not installed and the pump is restarted with the occluded tubing still installed, the initialization routine may be fooled into using the pressurized tubing to establish new baselines. This problem is referred to in the art as baseline "ratcheting."

Sensor drift may also interfere with proper occlusion detection. During infusion protocols having a very low infusion rate, the pump motor may actually run for very short period of time (e.g., one stepper motor "tick" or increment per minute). When the pump motor is not running, it may be assumed that increases in the downstream sensor signal are due to sensor drift, not to an actual build up in pressure caused by an occlusion in downstream tubing. Similarly, when the pump motor is not running, it may be assumed that decreases in the upstream sensor signal are due to sensor drift, not to an actual pressure decrease caused by an occlusion in upstream tubing. If the changes attributable to sensor drift are included in calculating the difference relative to the associated sensor baseline, false occlusion alarms may occur.

SUMMARY OF THE INVENTION

The present invention addresses the problems mentioned above and improves detection of occlusions in infusion pump systems. As may be understood, occlusion detection is made relative to upstream and downstream occlusion sensor baseline signals. The present invention helps ensure that proper baseline values are used as a reference so that occlusion detection avoids false positives without missing actual occlusion events.

In one aspect, the invention provides a method for making an antiratchet decision, whereby a determination is made each time the pump door is opened as to whether a new administration set (i.e. cassette and tubing) has been installed or a previous occluded administration set remains. Such an antiratchet decision is helpful in solving the "ratcheting" problem mentioned in the background because prior upstream and downstream sensor baselines may be kept if the antiratchet decision determines that the occluded administration set remains installed in the pump. Conversely, if the antiratchet decision finds a new administration set was installed, new sensor baselines may be established. In accordance with an embodiment of the present invention, the method includes calculating a baseline delta equal to a difference between the upstream sensor signal and the downstream sensor signal and comparing the baseline delta to a predetermined minimum baseline delta, wherein the antiratchet decision determines that occluded tubing was not replaced if the baseline delta is less than the minimum baseline delta. The minimum baseline delta may be determined based on historical baseline delta values stored by the infusion pump. The method may further include the step of comparing the downstream sensor signal to a predetermined downstream signal limit, wherein the antiratchet decision determines that occluded tubing was not replaced if the downstream sensor signal is greater than the downstream signal limit.

In another aspect, a method for adjusting an upstream sensor signal baseline to compensate for sensor signal drift is provided. Pursuant to this aspect, an upstream sensor signal baseline corresponding to fluid pressure equilibrium at the upstream sensor location is shifted in correspondence with decreases in the upstream sensor signal occurring while a pumping mechanism of the infusion pump is not operating.

The invention further encompasses an infusion pump programmed to implement the methodology of the present invention.

BRIEF DESCRIPTION OF THE DRAWING VIEWS

The invention is described in detail below with reference to the following figures.

DETAILED DESCRIPTION OF THE INVENTION

Figure 1:
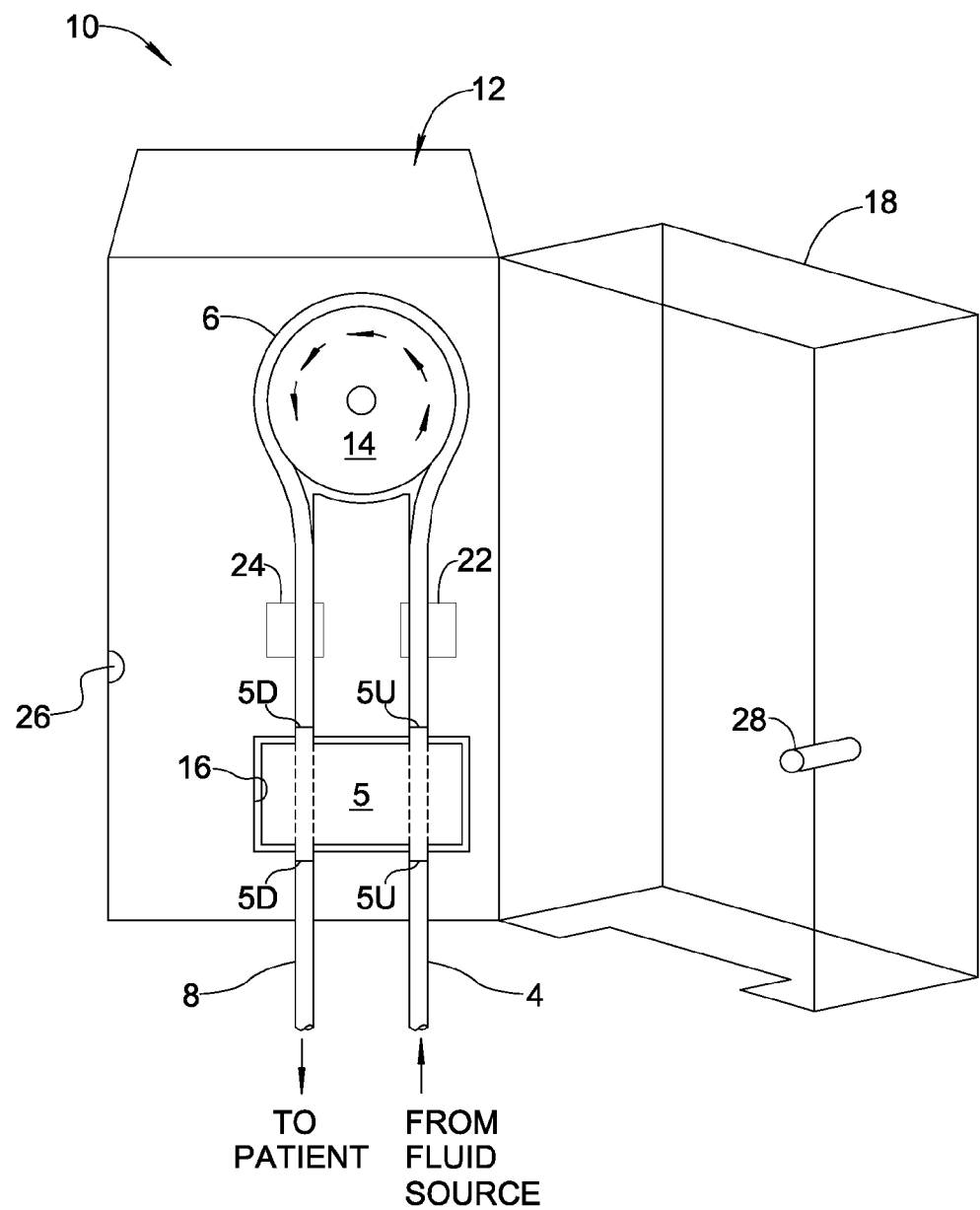
FIG. 1 is schematic representation of an infusion pump formed in accordance with an embodiment of the present invention, wherein a cassette and tubing are shown installed in the pump to illustrate basic operation.
Figure 2:
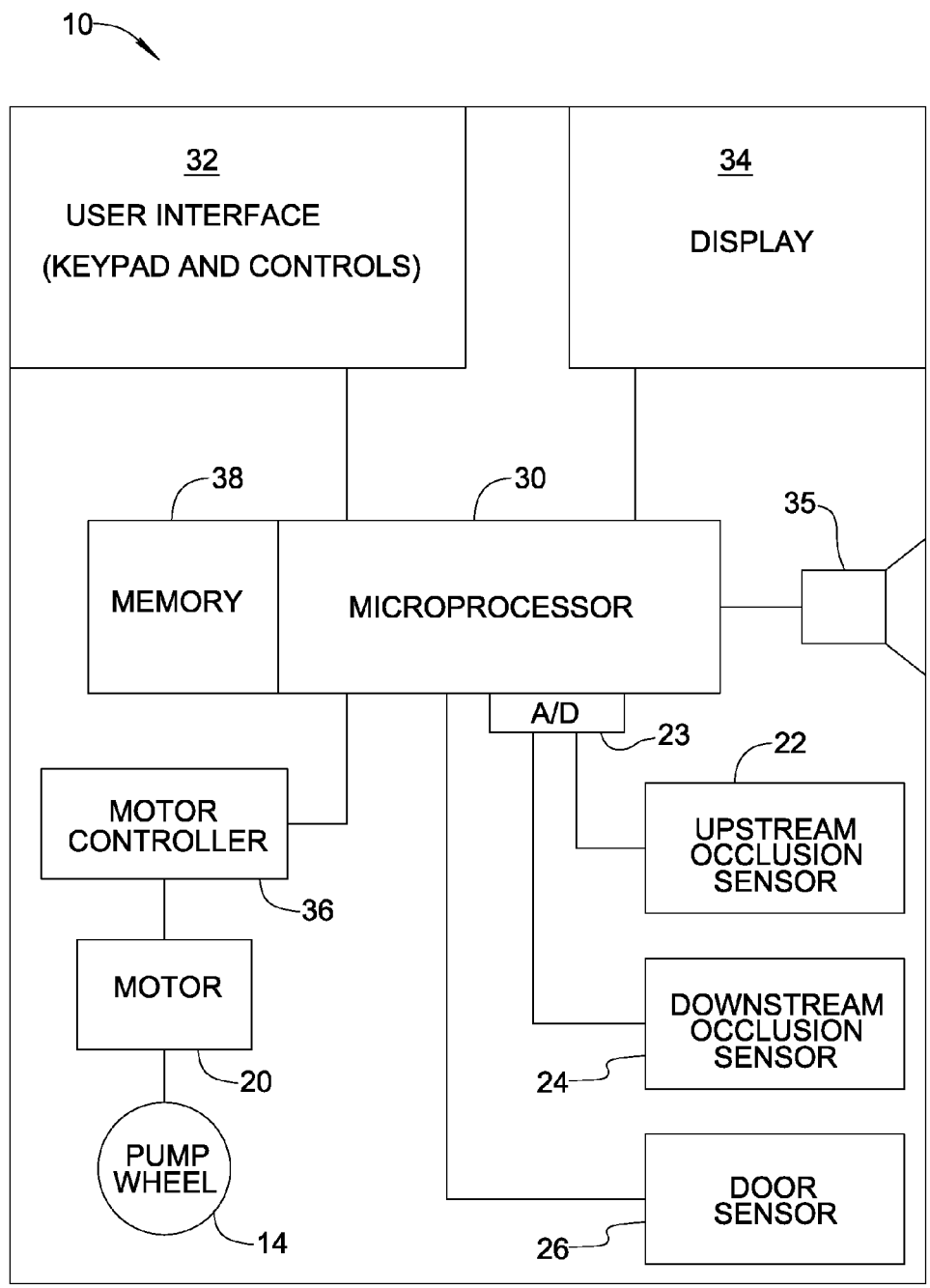
FIG. 2 is an electronic block diagram of the pump shown in FIG. 1.

FIGS. 1 and 2 schematically depict a programmable infusion pump 10 embodying the present invention. Infusion pump 10 includes a housing 12, a pump wheel or rotor 14 and a cassette receptacle 16 on an external face of the housing, and a door 18 connected to the housing to open and close over the cassette receptacle and pump wheel. As shown in FIG. 1, and administration set may be installed in association with the pump for carrying fluid from a fluid source to a patient. The administration set includes upstream tubing 4 running from the fluid source to the pump, downstream tubing 8 running from the pump to a patient, a cassette 5 received in cassette receptacle 16, and a U-shaped tubing segment 6 arranged around pump wheel 14. Cassette 5 is configured with connection terminals 5U and 5D for connecting upstream tubing 4 to an upstream end of tubing segment 6 and downstream tubing 8 to a downstream end of tubing segment 6 to complete a flow path from the upstream tubing to the downstream tubing via the pump.

Pump wheel 14 is part of a pumping mechanism operable to cause fluid flow through the tubing in an intended flow direction. The pumping mechanism further includes an electric motor 20 connected to pump wheel 14 and operable to rotate the pump wheel about its axis. Pump wheel 14 has radial fingers or rollers (not shown) that engage tubing segment 6 arranged about a circumferential portion of the wheel. When pump wheel 14 rotates, successive portions of tubing segment 6 are progressively squeezed to cause fluid to flow through the tubing in a flow direction toward the patient. The flow rate of infused fluid may be controlled by controlling the rate of motor 20. Those skilled in the art will understand that variations of the peristaltic pumping mechanism described above are possible. For example, motor 20 may drive a cam member connected to a series of parallel fingers or rollers arranged side-by-side, whereby peristaltic pumping action is applied to a straight segment of tubing instead of a curved segment of tubing as shown in FIG. 1. The present invention is not limited to a specific pumping mechanism configuration.

Infusion pump 10 is provided with an upstream occlusion sensor 22 at a location along tubing segment 6 upstream from pumping wheel 14 and a downstream occlusion sensor 24 at a location along tubing segment 6 downstream from pumping wheel 14. Upstream sensor 22 and downstream sensor 24 each provide a respective sensor signal indicative of a respective local fluid pressure in the tubing. For example, upstream and downstream sensors 22, 24 may be transducers or strain gauges arranged to engage an outer wall of tubing segment 6 to detect deflection of the flexible tubing wall caused by fluid pressure within the tubing and provide an electronic signal proportional to the deflection. In an embodiment of the present invention, each occlusion sensor 22, 24 may be configured to generate a voltage signal within a range from 0-2500 mV corresponding to local pressure in the tubing. Also by way of example, the occlusion sensors 22, 24 may be calibrated mechanically and via digital potentiometers for voltage offset and gain to establish an initial upstream baseline at 1250 mV, an initial downstream baseline at 750 mV, a differential of −5 psi from the upstream baseline at 950 mV (300 mV below the upstream baseline), a differential of +15 psi from the downstream baseline at 1150 mV (400 mV above the downstream baseline), and a differential of +18 psi from the downstream baseline at 1250 mV (500 mV above the downstream baseline).

Infusion pump 10 further includes a door sensor 26 arranged to cooperate with a trigger member 28 on door 18 to generate an electric signal indicating the current state of the door as either open or closed.

As seen in FIG. 2, infusion pump 10 is configured to permit a user to select or create, and then run, an infusion protocol determining the amount of fluid to be delivered to the patient and the rate at which the fluid is to be delivered. Infusion pump 10 includes a microprocessor 30 connected to a user interface 32 having input devices such as a keypad, switches and dial controls. Infusion pump 10 also includes a display 34 connected to microprocessor 30. Display 34 may be a touch screen display acting at times as part of user interface 32. Microprocessor 30 is connected to a motor controller 36 for driving electric motor 20 to administer a chosen protocol. One or more memory modules 38 are connected to or integrated with microprocessor 30 for storing instructions executable by the microprocessor for controlling pump operation. The stored instructions may be organized in software routines. Among the stored software routines are routines functioning to detect occlusions in accordance with the present invention. These routines are described in detail below. For purposes of the occlusion detection functionality, microprocessor 30 is connected to upstream occlusion sensor 22 and downstream occlusion sensor 24. Microprocessor 30 also receives the signal from door sensor 26. Analog-to-digital conversion circuitry 23 is shown for converting the analog voltage signals from the occlusions sensors and door sensor to digital form for use by microprocessor 30. Infusion pump 10 may also include an audible signal generator 35 connected to microprocessor 30.

Figure 3:
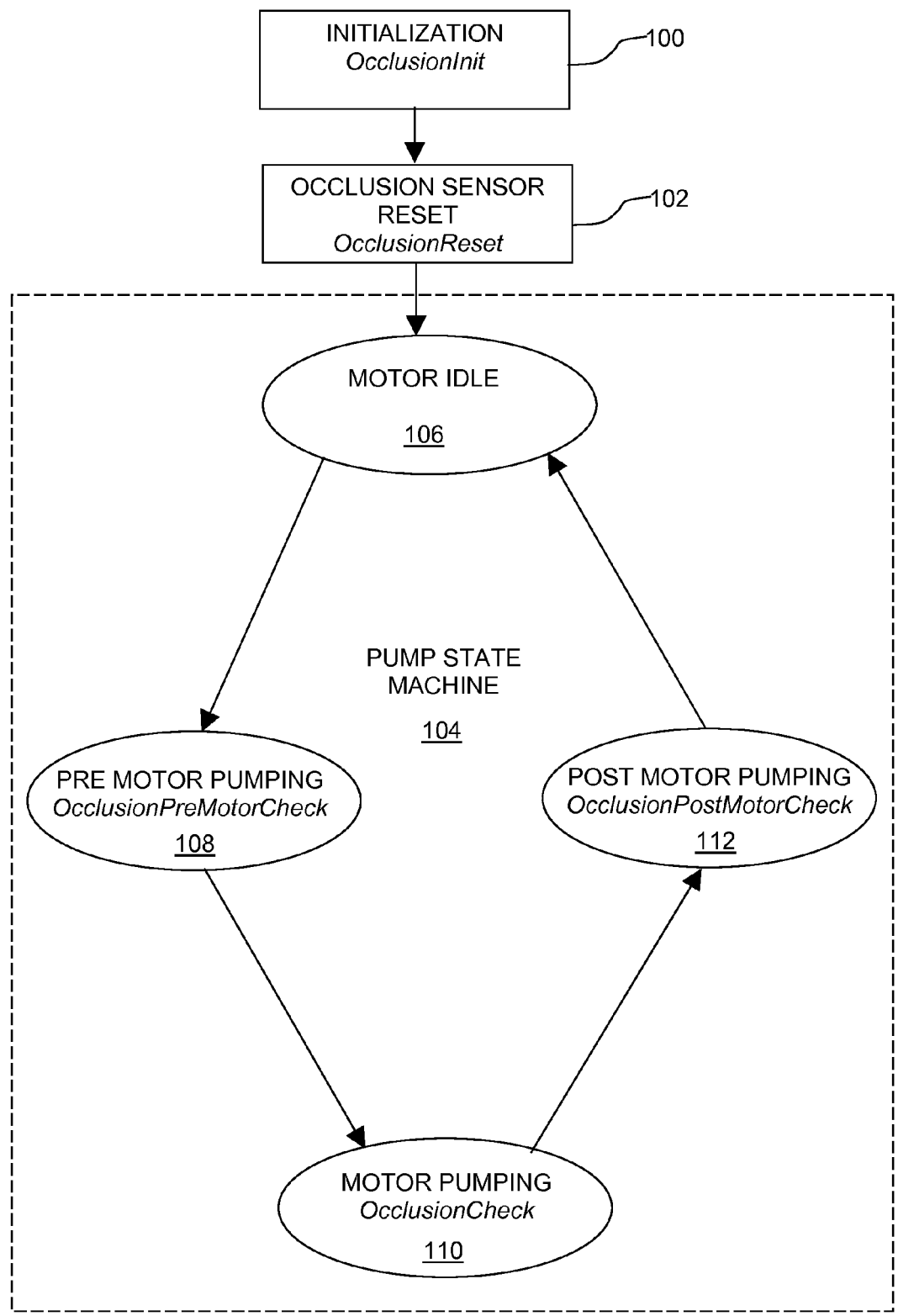
FIG. 3 is a schematic diagram generally illustrating occlusion detection software stored and executed by the pump in accordance with an embodiment of the present invention.

Attention is now directed to FIG. 3 generally illustrating occlusion detection software stored and executed by the pump in accordance with an embodiment of the present invention. In the embodiment shown, the logic for evaluating signals from upstream sensor 22 and downstream sensor 24 and determining when an occlusion is present is executed by various software routines synchronized with the activity of motor 20 though a pump state machine 104. Upon pump start-up, an initialization routine 100 ("OcclusionInit") is run. An occlusion sensor reset routine ("OcclusionReset") is run when a therapy protocol or pump priming is started. Then, the pump state machine 104 manages execution based on the state of pump 10. Pump 10 has a motor idle state 106 in which motor 20 is not pumping. The selected protocol program determines when motor 20 should be activated and deactivated to achieve the desired flow rate for the protocol. Under pump state machine 104, when the pump is in a pre-motor state 108 just prior to activation of motor 20, a pre-motor routine ("OcclusionPreMotorCheck") is called. While pump 10 is in a motor pumping state 110 wherein motor 20 is activated and pumping fluid, state machine 104 handles occlusion detection according to a main occlusion check routine ("OcclusionCheck"). As soon as motor 20 is deactivated and leaves pumping state 110, the pump enters a post-motor state 112 wherein occlusion detection logic is handled by a post-motor routine ("OcclusionPostMotorCheck"). The occlusion detection software runs periodically whenever new upstream and downstream signal values are available from analog-to-digital converters 23, for example every 250 ms. The readings from analog-to-digital converters 23 may be synchronized with motor ticks so data are sampled more frequently when the motor is running at a higher rpm rate.

Figure 4:
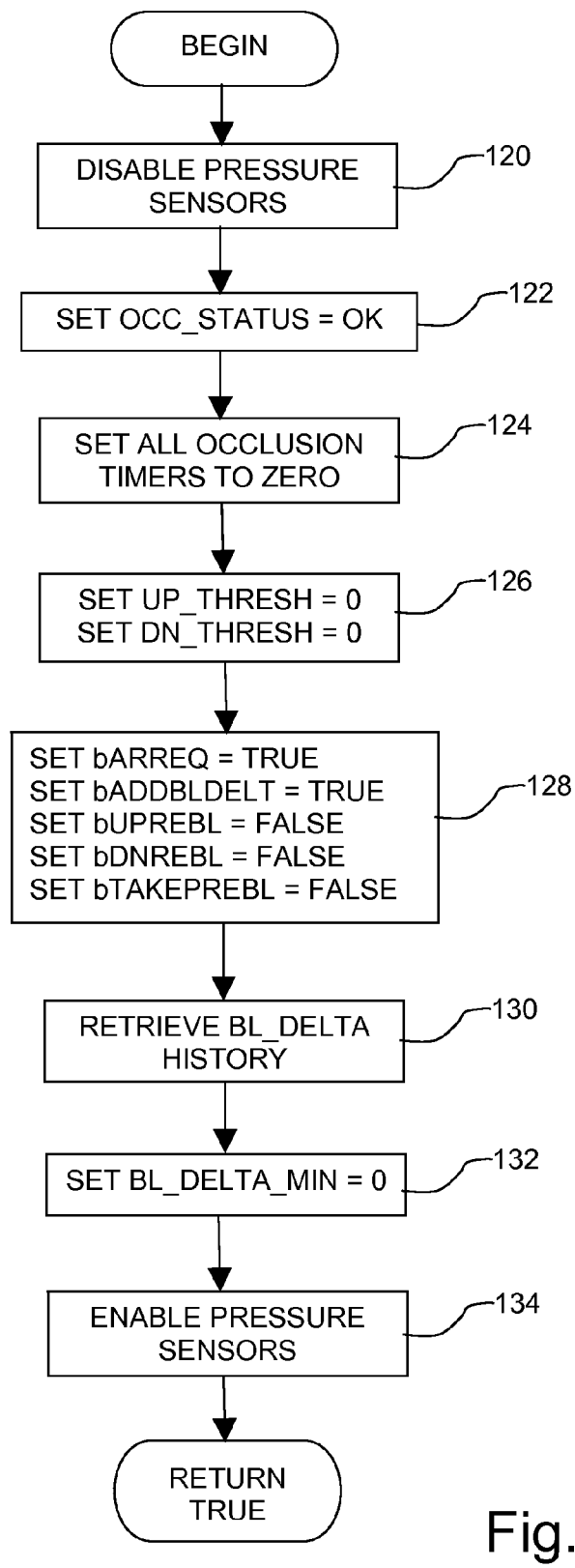
FIG. 4 is a flow diagram of a pump initialization routine in accordance with an embodiment of the present invention.

The OcclusionInit routine is illustrated in FIG. 4. In block 120, occlusion sensors 22 and 24 are temporarily disabled. Block 122 sets the value of an occlusion status variable OCC_STATUS to a value indicating there is no occlusion (e.g. "OK"), and block 124 sets all occlusion timers to zero. As will be explained later, the occlusion timers track how long a particular occlusion signal has exceeded a predetermined threshold representing a difference from the occlusion sensor baseline. In block 126, the upstream and downstream occlusion signal threshold variables, namely UP_THRESH and DN_THRESH, are set to zero. UP_THRESH tracks the difference of the upstream occlusion sensor signal relative to the upstream sensor baseline, and DN_THRESH tracks the difference of the downstream occlusion sensor signal relative to the downstream sensor baseline. In essence, block 126 causes a new respective baseline to be established for each occlusion sensor that is equivalent to the current sensor signal value. In block 128, Boolean variable are set to initial values. These include bARREQ and bADDBLDELT, which are set to TRUE. These also include bUPREBL, bDNREBL, and bTAKEPREBL, which are set to FALSE. The significance of these variables will become apparent later in this description. Pursuant to block 130, historical "baseline delta" data is retrieved from memory 38. The baseline delta is defined as the difference between the upstream signal baseline and the downstream signal baseline. A variable designated BL_DELTA_MIN is set to zero in block 132. Finally, in block 134, occlusion sensors 22 and 24 are enabled. Upon completion, OcclusionInit, which may be a Boolean function, returns a TRUE value.

Figure 5A:
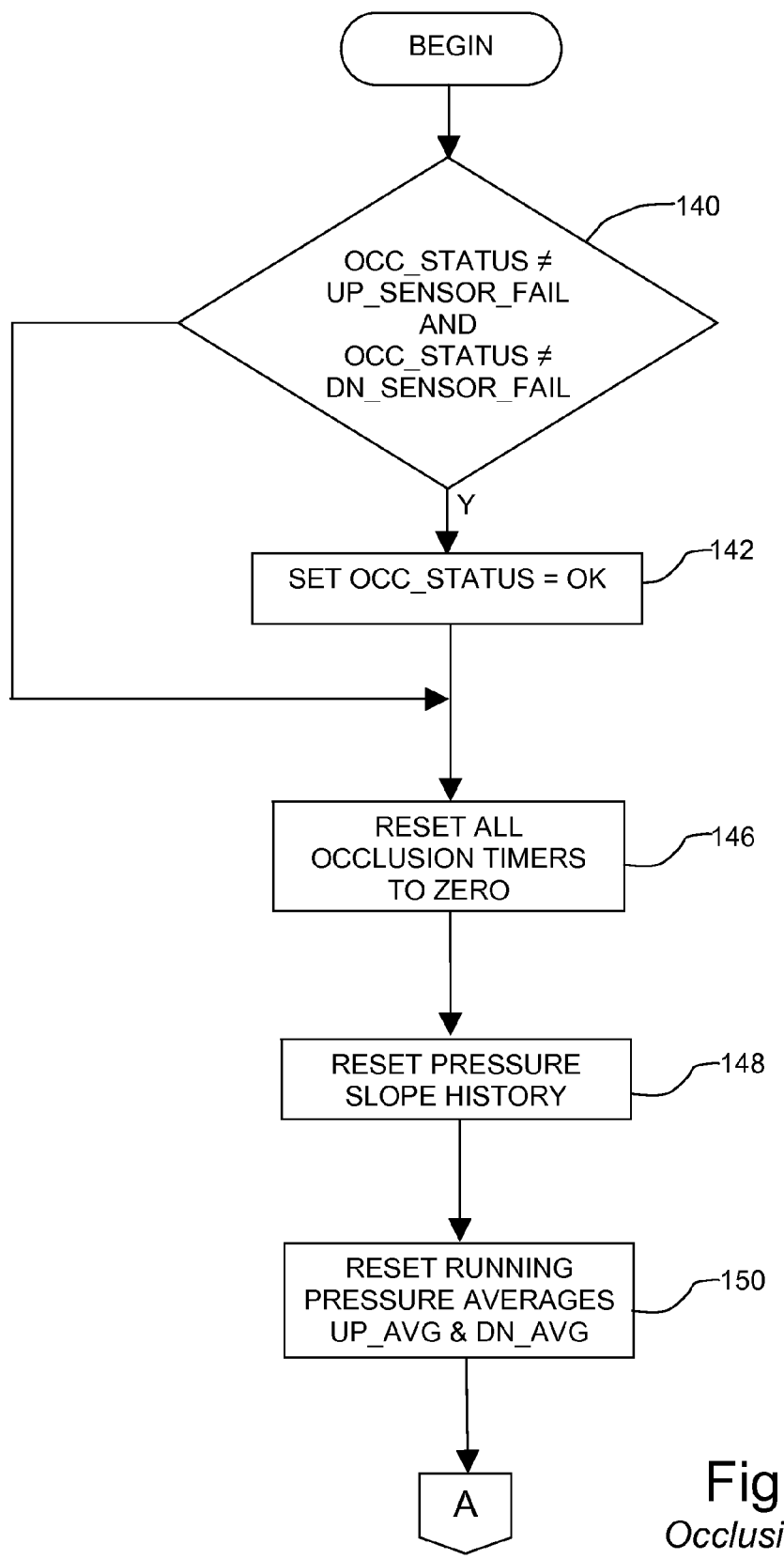
FIGS. 5A-5B are a flow diagram of a pump reset routine in accordance with an embodiment of the present invention.
Figure 5B:
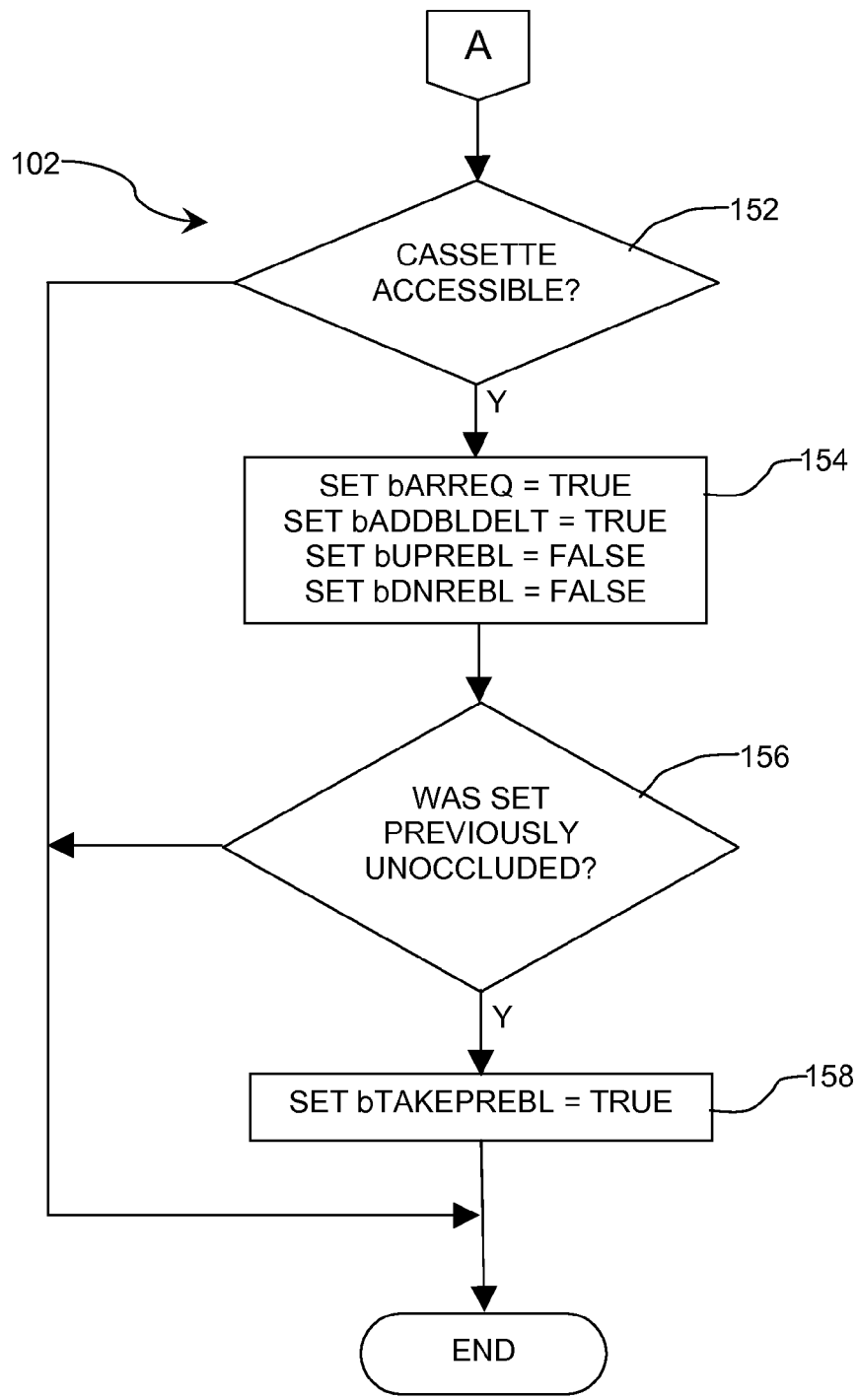

The OcclusionReset routine is shown in FIGS. 5A and 5B. Decision block 140 checks whether a previous sensor failure has occurred. If no sensor failure has occurred, the value of OCC_STATUS is reset to OK by block 142. Variables that are specifically not reset include the previous thresholds UP_THRESH and DN_THRESH, LAST_UP and LAST_DN corresponding to the last sampled signal values from upstream sensor 22 and downstream sensor 24 before the motor last stopped, and a motor tick counter for counting rotational increments of motor 20. Block 146 resets all occlusion timers to zero. In block 148, the slope history of the upstream and downstream pressure sensor signals is reset. In block 150, variables UP_AVG and DN_AVG for keeping running averages of the sampled upstream and downstream sensor signals are reset.

The OcclusionReset routine then proceeds to a decision block 152 that directs flow based on whether cassette 5 was accessible while the pump was stopped. The cassette was accessible if door sensor 26 indicates that door 18 was opened after the pump was stopped. If not, then OcclusionReset ends. If the cassette was accessible, there is a possibility that a new cassette and administration set were installed, and flow proceeds to block 154 to reset Boolean variables bARREQ, bADDBLDELT, bUPREBL, and bDNREBL as indicated. Decision block 156 then determines if the administration set was unoccluded when the pump was last stopped by checking the value of OCC_STATUS. If there was no prior occlusion, it may be assumed that a ratcheting problem does not exist, and the Boolean variable bTAKEPREBL is set to TRUE in block 158 so that new occlusions sensor baselines will be established. Execution of OcclusionReset is then complete.

Figure 6A:
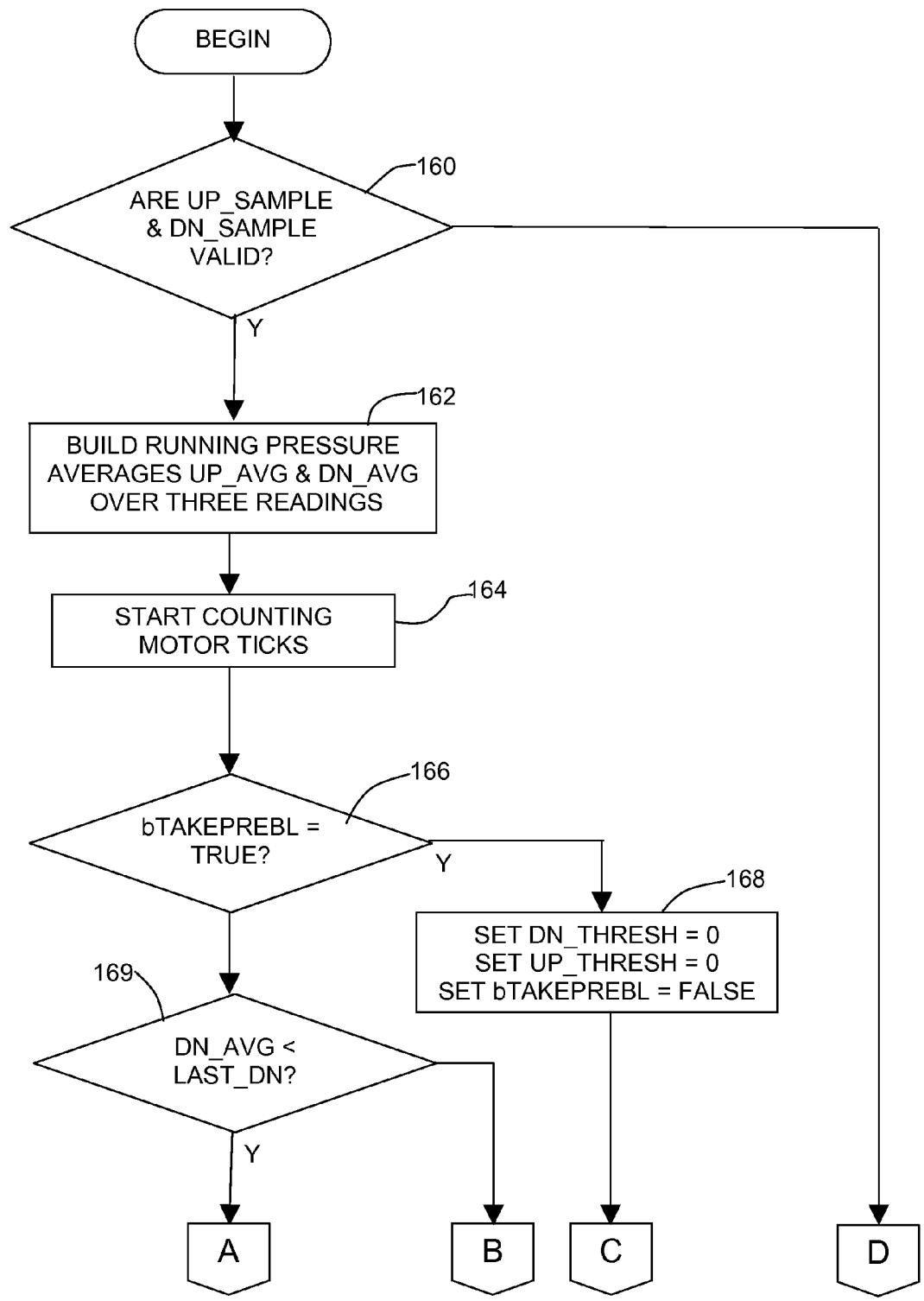
FIGS. 6A-6B are a flow diagram of an occlusion pre-motor check routine in accordance with an embodiment of the present invention.
Figure 6B:
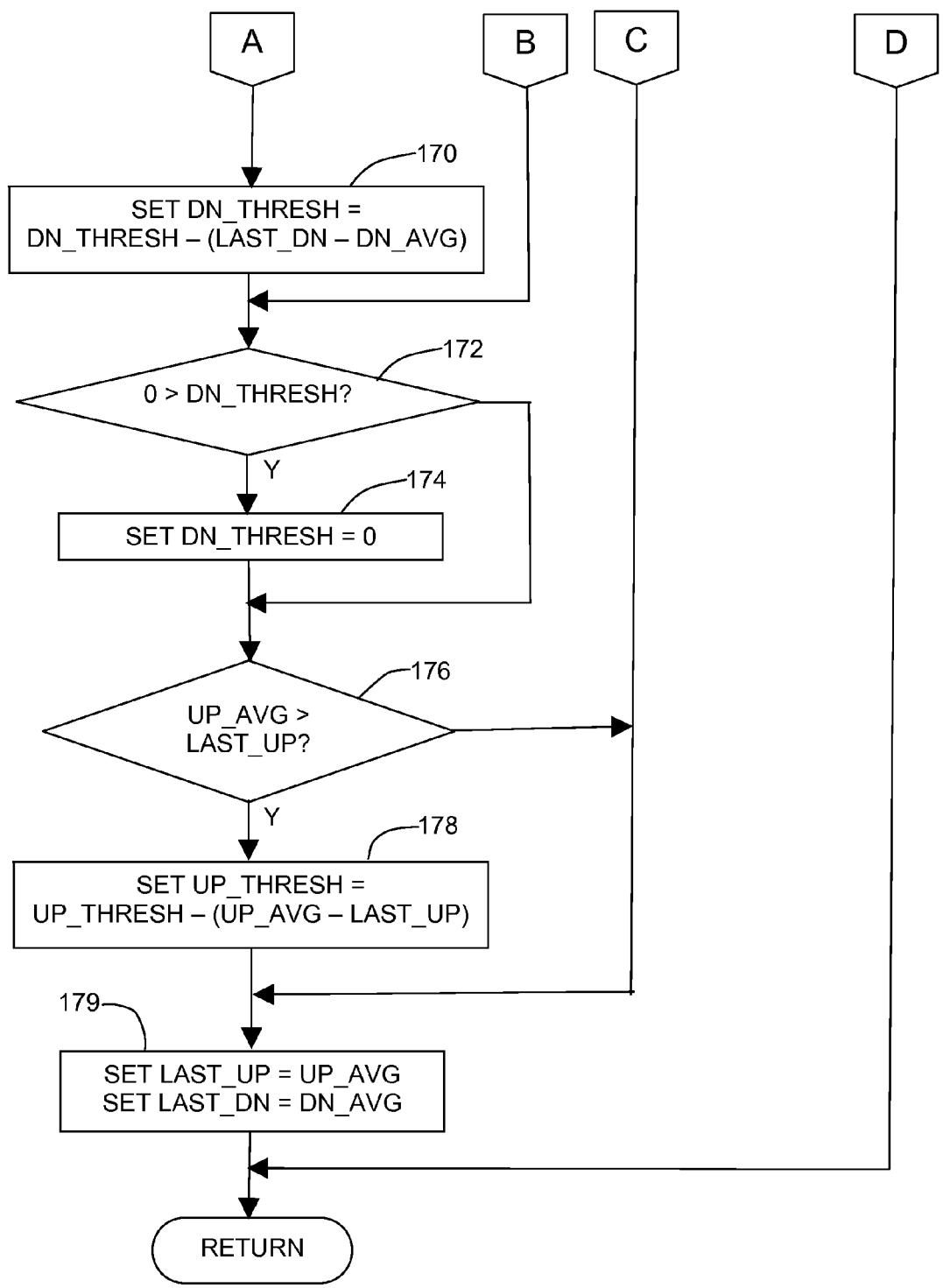

FIGS. 6A-6B illustrate the OcclusionPreMotorCheck routine. An initial decision block 160 ensures that execution proceeds only when the currently sampled upstream sensor signal UP_SAMPLE and downstream sensor signal DN_SAMPLE are considered valid. For example, the UP_SAMPLE and DN_SAMPLE readings may compared to a predetermined maximum or upper limit. If UP_SAMPLE and DN_SAMPLE are valid, the routine builds running averages UP_AVG and DN_AVG of the upstream and downstream sensor signal values in accordance with block 162. For example, the running averages UP_AVG and DN_AVG may be calculated for the last three sampled readings from upstream sensor 22 and downstream sensor 24, respectively, and are continuously updated as new sensor readings are sampled. In block 164, the motor tick counter is started in order to register motor ticks.

Decision block 166 branches flow based on whether Boolean variable bTAKEPREBL is TRUE or FALSE. The value of bTAKEPREBL determines whether new sensor baselines are established. If the cassette was previously accessible but there was no prior occlusion, then bTAKEPREBL will be set to TRUE. If decision block 166 finds bTAKEPREBL equals TRUE, then thresholds UP_THRESH and DN_THRESH are set to zero in block 168, in effect establishing UP_AVG and DN_AVG as the respective sensor baselines. Also in block 168, the value of bTAKEPREBL is changed from TRUE to FALSE. Flow then jumps to block 179, wherein LAST_UP and LAST_DN are set equal to UP_AVG and DN_AVG, respectively.

If decision block 166 finds bTAKEPREBL is FALSE, then the current baselines are maintained but may be adjusted to account for possible drift in the upstream and downstream sensor signals while the motor was inactive. If the voltage signal from downstream sensor 24 increased while motor 20 was off, it may be assumed that the signal change is attributable to sensor signal drift, not to actual pressure change. Consequently, the value of DN_THRESH representing the current pressure signal difference relative to the downstream sensor baseline is not changed to reflect increases in the downstream sensor signal while the motor was off. In essence, this is the same as adjusting the downstream baseline to account for drift. If an increase in downstream pressure occurs, decision block 169 has a NO result and flow skips to decision block 172. If, on the other hand, the downstream sensor signal decreases while motor 20 is inactive, it may be assumed that some pressure was released and the DN_THRESH should be adjusted to reflect the decrease in pressure. For this situation, decision block 169 gives a YES result and DN_THRESH is adjusted in accordance with block 170. Pursuant to decision block 172 and block 174, if the adjustment of DN_THRESH results in a negative value, DN_THRESH is set to zero. In other words, DN_THRESH is not allowed to be go negative.

Change in upstream threshold UP_THRESH is handled by blocks 176 and 178. Decision block 176 determines if the upstream pressure signal increased while the motor was off. If not, and instead there was a decrease in pressure while motor was off, the decrease is assumed to be the result of sensor signal drift and not the result of an actual pressure decrease (a vacuum increase). In this case, decision block 176 has a NO result and UP_THRESH is kept where it is despite the pressure signal change, in essence shifting the upstream baseline to account for sensor drift. Flow skips to block 179. However, if decision block 176 finds that the upstream sensor signal increased while the motor was off, it is assumed that some vacuum was released and UP_THRESH is adjusted in block 178. The upstream threshold UP_THRESH is allowed to go negative; this ensures that a high pressure that lingers for a while after door 18 was closed does not cause false baseline adjustments.

Finally, as indicated by block 179, OcclusionPreMotorCheck sets LAST_UP and LAST_DN equal to the respective running averages UP_AVG and DN_AVG.

Figure 7:
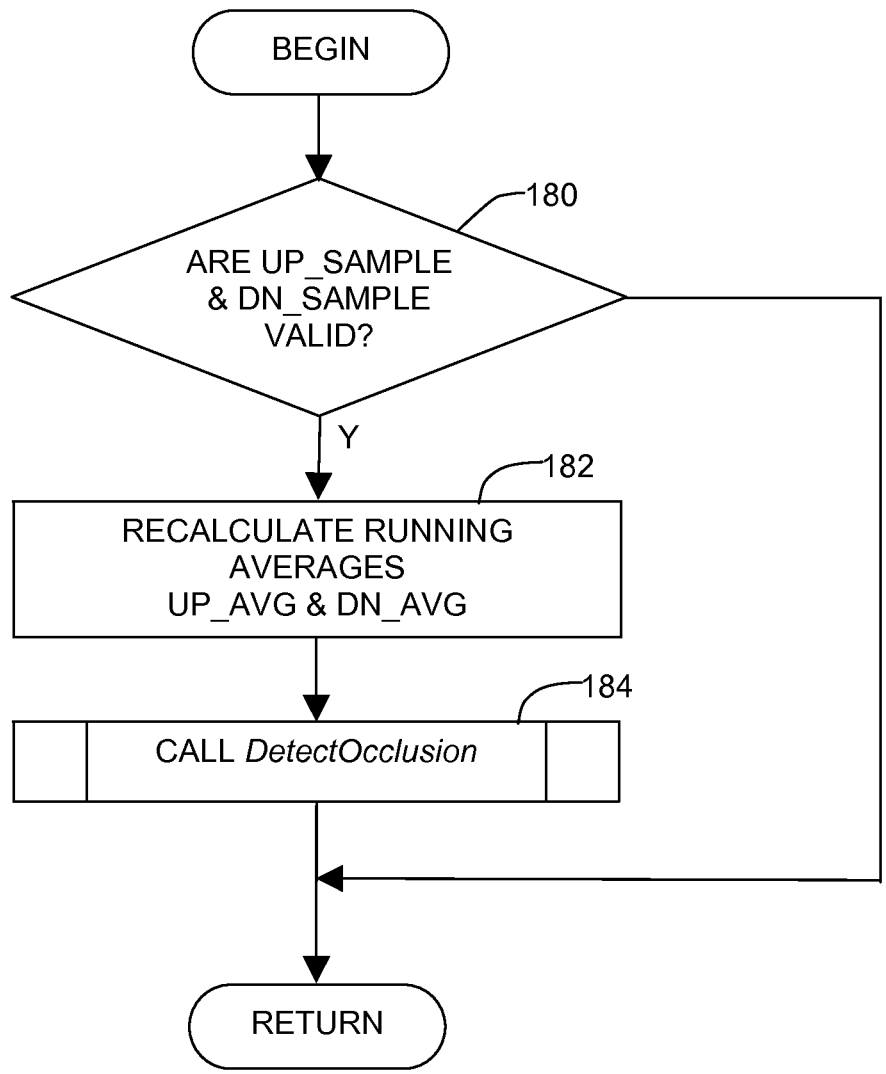
FIG. 7 is a flow diagram of an occlusion check routine in accordance with an embodiment of the present invention.

FIG. 7 illustrates the flow of the OcclusionCheck routine corresponding to motor pumping state 110. An initial decision block 180 checks that the currently sampled sensor signals UP_SAMPLE and DN_SAMPLE are considered valid. Block 182 recalculates the running averages UP_AVG and DN_AVG. Finally, block 184 calls another routine, DetectOcclusion, that determines if an occlusion is present in the tubing. The DetectOcclusion routine is described in detail below with reference to FIGS. 9A-9G.

Figure 8:
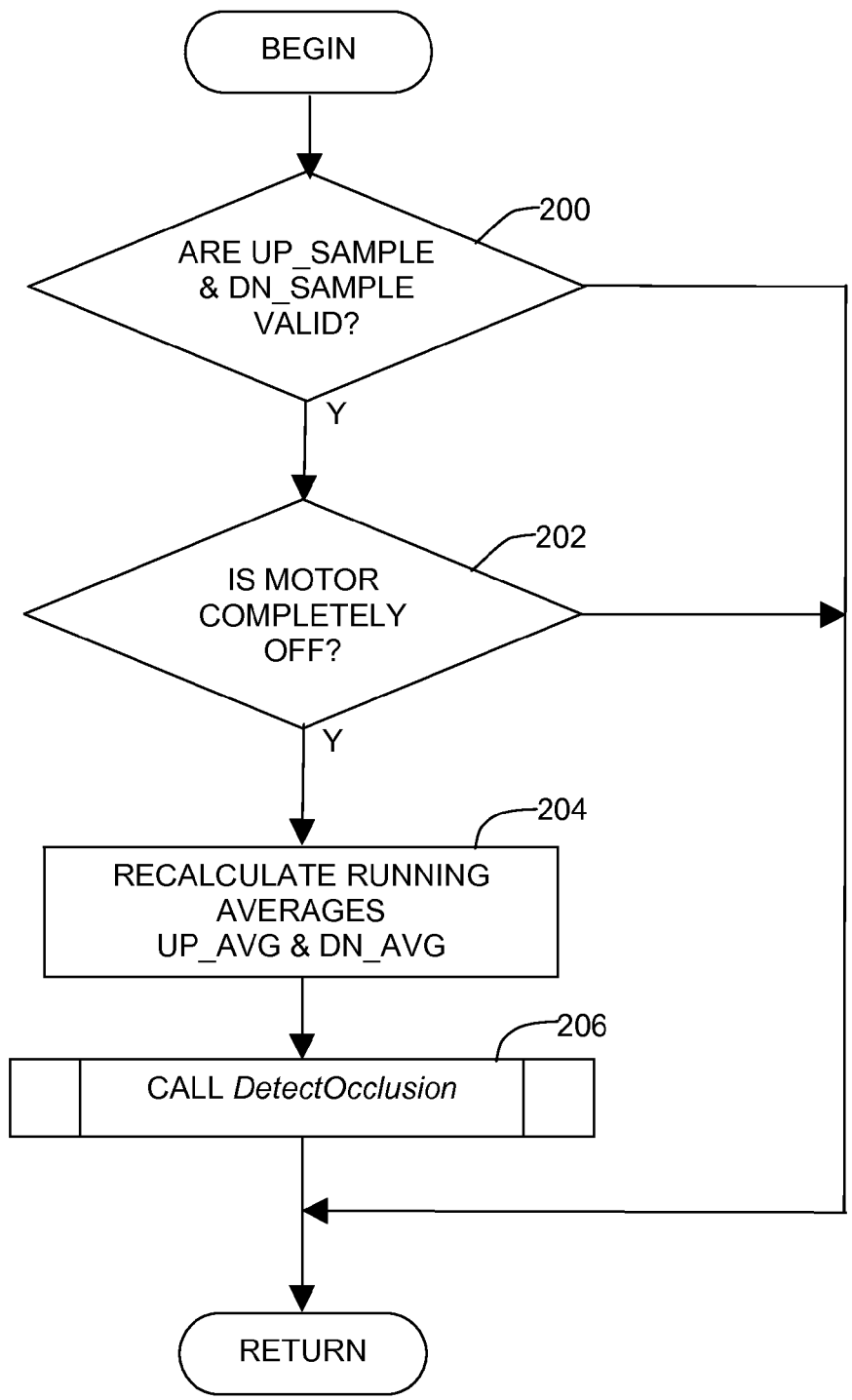
FIG. 8 is a flow diagram of an occlusion post-motor check routine in accordance with an embodiment of the present invention.

The PostMotorCheckRoutine corresponding to post-motor state 112 is diagrammed in FIG. 8 and is largely similar to the OcclusionCheck routine. An initial decision block 200 checks that the currently sampled sensor signals UP_SAMPLE and DN_SAMPLE are considered valid. Another decision block 202 ensures that motor 20 is completely off by checking the state of motor controller 36. Block 204 recalculates the running averages UP_AVG and DN_AVG. Finally, block 206 calls the DetectOcclusion routine.

The DetectOcclusion routine will now be described in association with FIGS. 9A-9G. Block 220 sets UP_SLOPE and DN_SLOPE, variables for tracking the slope of the upstream and downstream sensor signals, to zero. Block 220 also sets UP_DIFF and DN_DIFF to zero; these variables are used to store respective upstream and downstream pressure changes since the last occlusion check. In block 222, the number of motor ticks since the last occlusion check is determined. Block 224 calculates UP_DIFF as equal to LAST_UP minus UP_SAMPLE, and DN_DIFF as equal to DN_SAMPLE minus LAST_DN. The calculated pressure differences are then added to the respective occlusion thresholds in accordance with block 226. Decision block 228 and block 230 prevent the downstream threshold DN_THRESH from going negative, in effect shifting the downstream baseline downward.

Figure 9A:
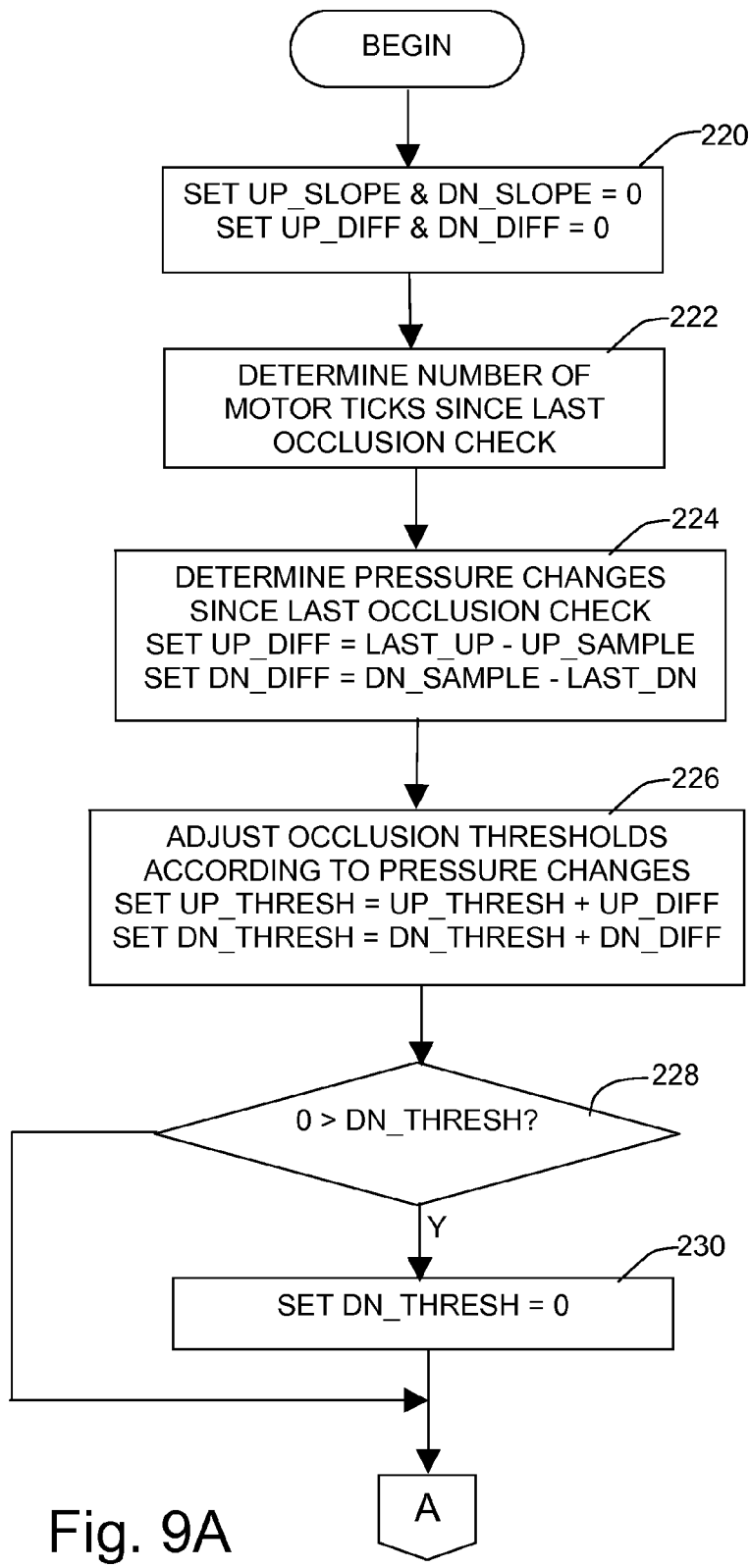
FIGS. 9A-9G are a flow diagram of a detect occlusion routine called by the occlusion check routine of FIG. 7 and the occlusion post-motor check routine of FIG. 8 in accordance with an embodiment of the present invention.
Figure 9B:
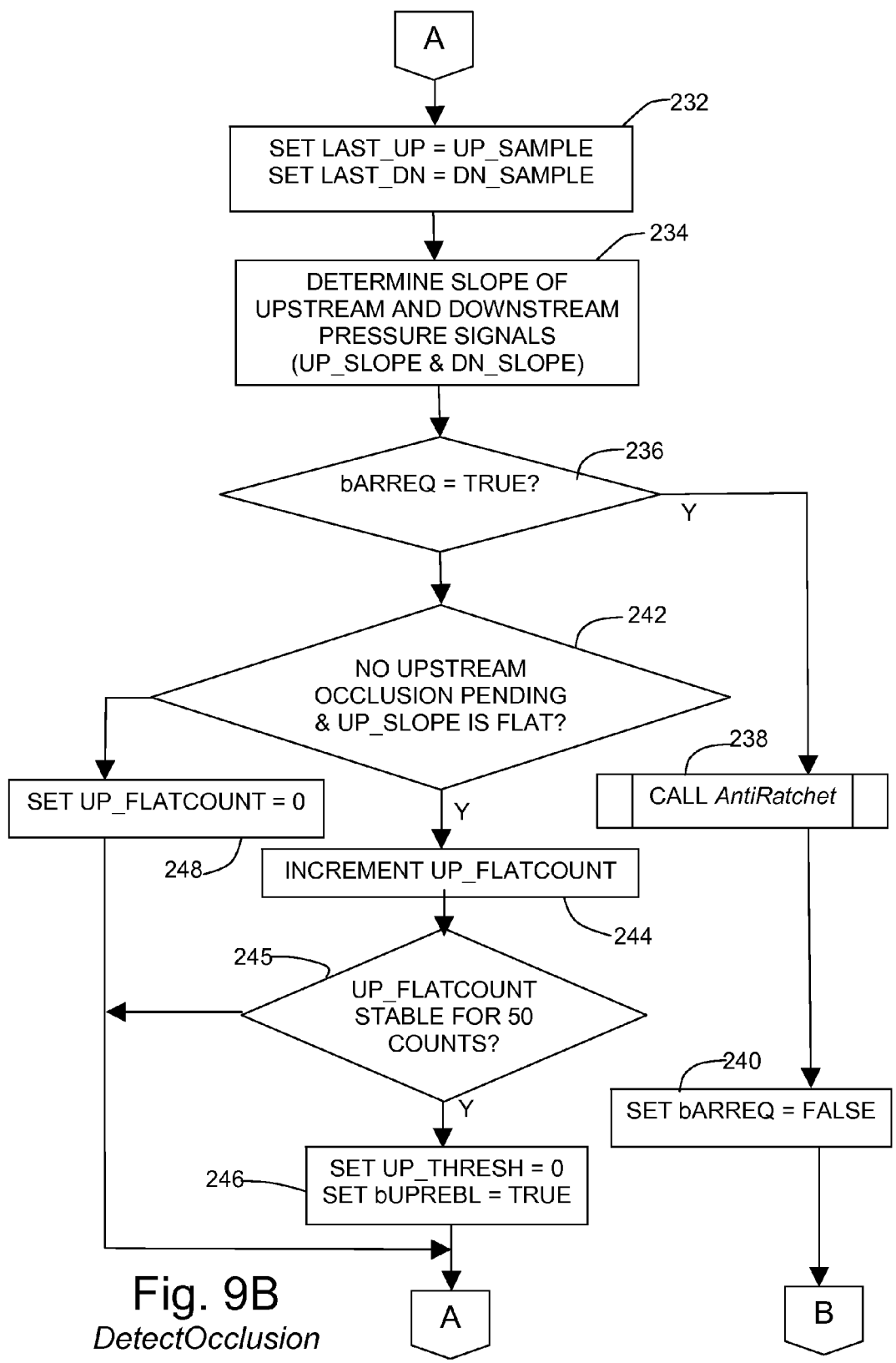

Moving to FIG. 9B, in block 232, the current sensor signal values are kept as LAST_UP and LAST_DN for later reference. Pursuant to block 234, the signal slopes UP_SLOPE and DN_SLOPE are calculated over the last full motor rotation using pressure difference data stored in a slope history buffer. By way of example, in the present embodiment, one full motor rotation would correspond to twelve motor ticks. Next, in decision block 236, the Boolean variable bARREQ is referenced to determine if the AntiRatchet routine should be called. If bARREQ is TRUE, then flow branches to block 238 in which the AntiRatchet of FIGS. 10A-10B routine is called. After the call to AntiRatchet, bARREQ is set to FALSE in block 240. If decision block 236 finds bARREQ is FALSE, then flow proceeds to decision block 242 for further logic used to apply sensor drift compensation. If the upstream sensor signal slope is substantially flat and there is no upstream occlusion pending (pendency of an occlusion is described later in connection with FIGS. 14 and 15), then a variable UP_FLATCOUNT tracking consecutive times UP_SLOPE is below a slope threshold (is substantially flat) is incremented in block 244 and flow proceeds to decision block 245. If UP_FLATCOUNT is greater than or equal to a chosen threshold (e.g. 50) indicating stability in the slope, then the current upstream pressure signal can serve as the new upstream baseline by setting UP_THRESH equal to zero in block 246. Further in block 246, Boolean variable bUPREBL is set to TRUE to indicate that the upstream sensor has been rebaselined. On the other hand, if decision block 242 gives a NO result, rebaselining of the upstream sensor is bypassed and UP_FLATCOUNT is set to zero in block 248. Continuing to FIG. 9C, it will be understood that decision block 250, block 251, decision block 252, block 253, and block 254 are analogous to decision block 242, block 244, decision block 245, block 246, and block 248, respectively, but apply to the downstream sensor and downstream threshold.

Figure 11:
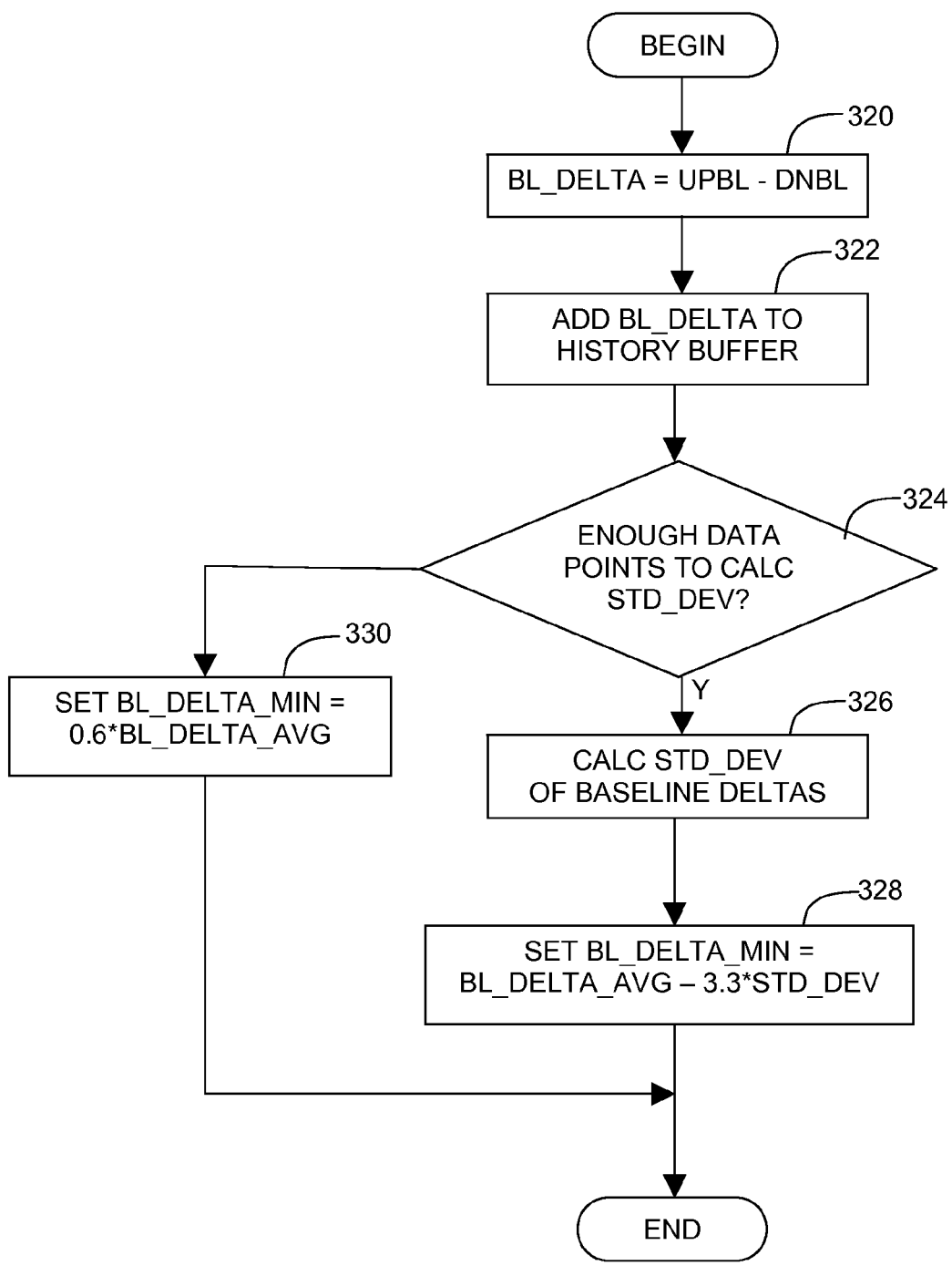
FIG. 11 is a flow diagram of an occlusion baseline delta routine called by the detect occlusion routine of FIGS. 9A-9G in accordance with an embodiment of the present invention.

Decision block 256 allows for the addition of a new baseline delta value to the baseline delta history buffer if both the upstream sensor and downstream sensor have been rebaselined as indicated by Boolean variables bUPREBL and bDNREBL, and if Boolean variable bADDBLDELT is TRUE. If these conditions are met, block 258 sets bADDBLDELT to FALSE and block 260 calls a routine OccBaselineDelta to add a baseline delta value to the history buffer and calculate the minimum baseline delta BL_DELTA_MIN initialized in block 132 of the OcclusionInit routine and used by the AntiRatchet routine. The OccBaselineDelta routine is illustrated in FIG. 11 and begins with block 320 calculating the baseline delta BL_DELTA as equal to the upstream baseline UPBL minus the downstream baseline DNBL. In block 322, BL_DELTA is added to the history buffer. Blocks 324 through 330 are programmed to determine a suitable value for BL_DELTA_MIN based on the historical baseline delta information for the pump. In the embodiment described herein, the determination of BL_DELTA_MIN may depend upon how much historical baseline delta information is available in the history buffer. For example, if there are at least some chosen number of baseline delta values in the history buffer to calculate a meaningful standard deviation of the data, e.g. at least twenty values, then decision block 324 directs calculation of BL_DELTA_MIN in accordance with blocks 326 and 328, wherein BL_DELTA_MIN is set equal to the average of the historical baseline delta values BL_DELTA_AVG minus 3.3 times the standard deviation of the baseline delta values. If there are fewer than the chosen threshold number of historical baseline delta values, decision block 324 directs flow to block 330 which sets BL_DELTA_MIN equal to 0.6 times BL_DELTA_AVG.

Figure 9C:
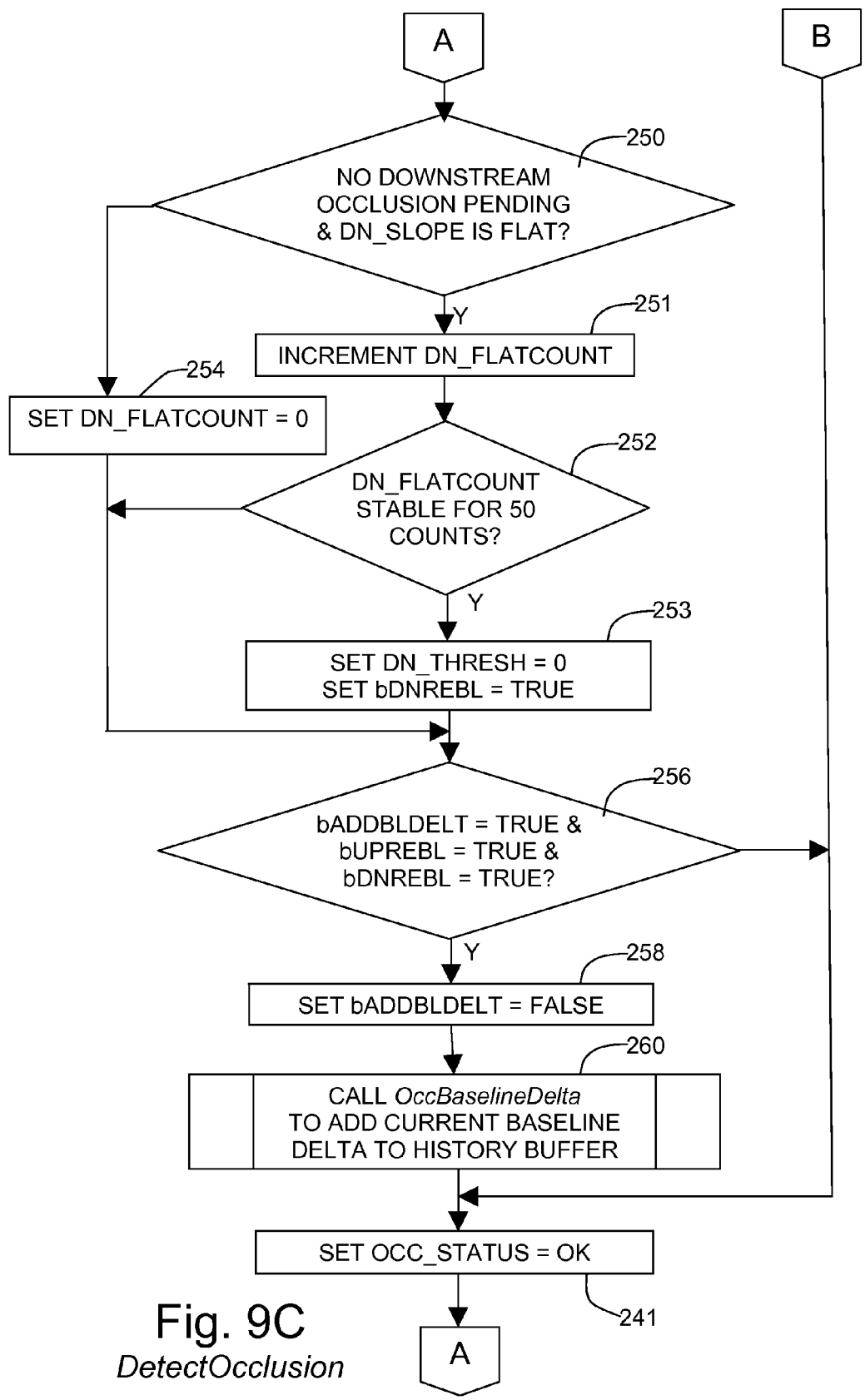
Figure 12A:
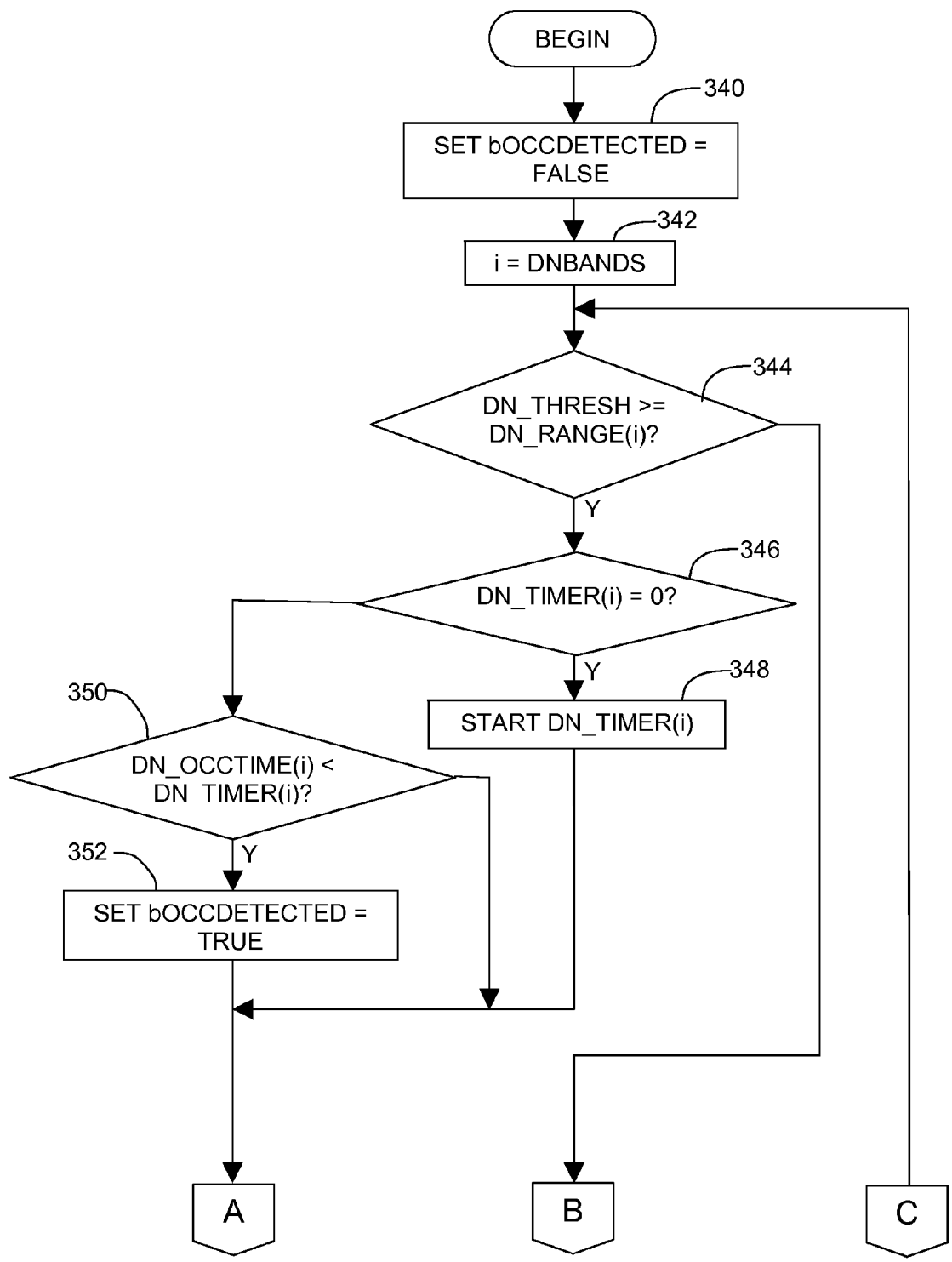
FIGS. 12A-12B are a flow diagram of a downstream occlusion detected routine called by the detect occlusion routine of FIGS. 9A-9G in accordance with an embodiment of the present invention.
Figure 12B:
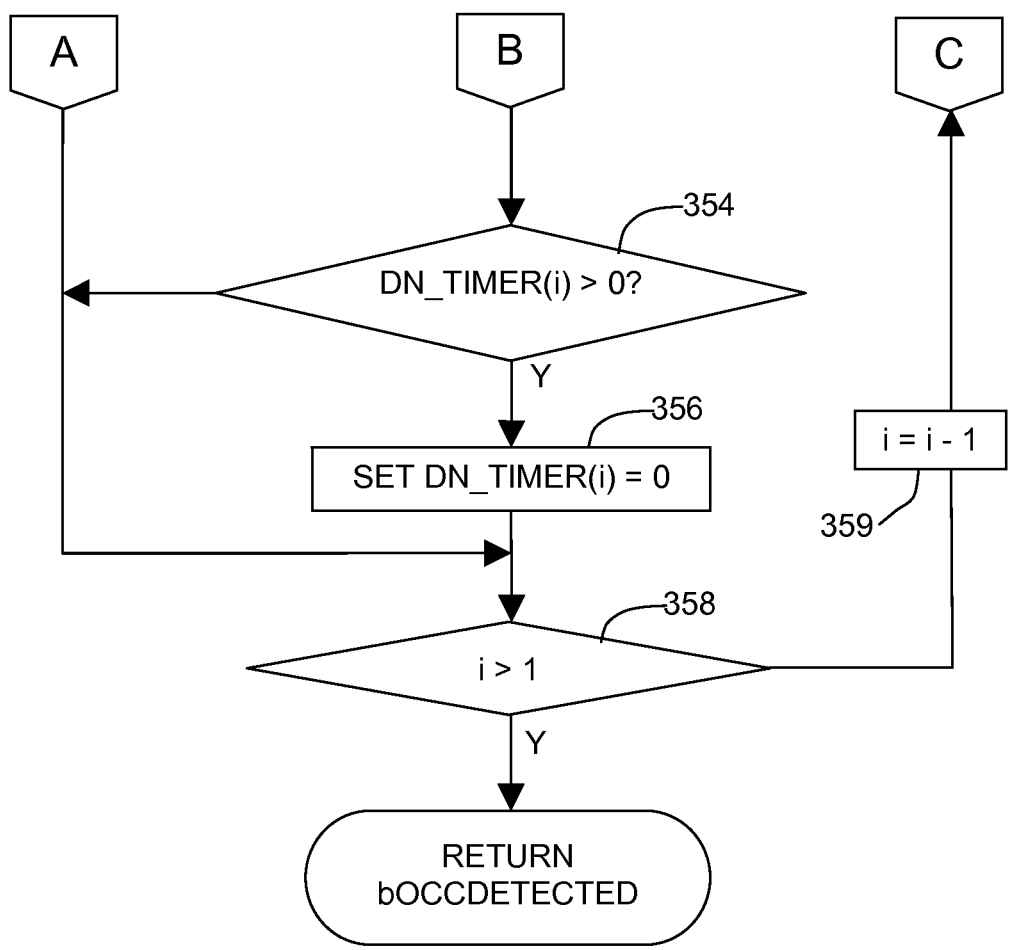

Attention is directed back to FIG. 9C. Flow continues at block 242 to set OCC_STATUS to OK. Progressing to FIG. 9D, decision block 262 determines if there is a downstream occlusion by executing a Boolean output routine DownstreamOcclusionDetected that returns TRUE if a downstream occlusion is found. The logic of DownstreamOcclusionDetected is set forth in FIGS. 12A-12B. In the present embodiment, a downstream occlusion is detected if the downstream pressure reading rises 15 psi above the downstream baseline and remains above this level for 30 seconds, or if the downstream pressure reading rises 18 psi above the downstream baseline and remains above this level for 5 seconds. The two timed criteria are referred to herein as occlusion "bands." The logic of FIGS. 12A-12B is configurable to evaluate one or more occlusion bands depending upon design choice. In the example embodiment now described, there are two downstream occlusion bands, however only one occlusion band may be used (this is the case for the upstream occlusion detection scheme described below) or more than two occlusion bands may be used. In FIGS. 12A-12B, flow is iterative from one band to the next; the particular occlusion band is tracked by an indexing integer "i" and the total number of downstream occlusion bands is stored as a parameter DNBANDS. The pressure level or threshold for occlusion in a given band "i" is stored as DN_RANGE(i). Thus, in the present example, DN_RANGE(1) corresponds to 15 psi, DN_RANGE(2) corresponds to 18 psi, and DNBANDS=2. Respective timers for each band are designated DN_TIMER (i), and the respective time limits for each band are stored as DN_OCCTIME(i). Consequently, in the present example, DN_OCCTIME(1) is 30 seconds and DN_OCCTIME(2) is 5 seconds.

DownstreamOcclusionDetected sets an occlusion detection Boolean variable bOCCDETECTED to FALSE in block 340. This variable will be changed to TRUE if occlusion is detected in accordance with the criteria of at least one occlusion band. Index counter "i" is initialized by block 342 to equal the total number of downstream bands DNBANDS, thereby starting evaluation of the outermost occlusion band. Decision block 344 checks if the downstream threshold DN_THRESH has reached or exceeded DN_RANGE(i). If so, decision block 346 checks whether DN_TIMER(i) is at zero. If DN_TIMER(i) is at zero, block 348 starts DN_TIMER(i). If, however, DN_TIMER(i) is already counting (not at zero), then decision block 350 compares DN_TIMER(i) to DN_OCCTIME(i). If DN_TIMER(i) exceeds the band time limit DN_OCCTIME(i), then a downstream occlusion is detected and block 352 sets bOCCDETECTED to TRUE. If decision block 344 finds that DN_THRESH has not reached or exceeded DN_RANGE(i), then flow proceeds directly to decision block 354 to check if DN_TIMER(i) is greater than zero. If it is, then DN_TIMER(i) is reset to zero in block 356. Decision block 358 determines if there are more occlusion bands to evaluate. If the index counter "i" is greater than 1, then "i" is decremented by 1 in block 359 and flow returns to decision block 344 to repeat the logic for the next downstream occlusion band. If the index counter "i" equals 1, then all downstream occlusion bands have been evaluated and the value of bOCCDETECTED is returned by the routine.

Returning now to decision block 262 of the DetectOcclusion routine, if a downstream occlusion was detected, any alarm is suppressed until the AntiRatchet routine has had a chance to run. This is done by checking the value of bARREQ in decision block 264. If bARREQ is FALSE, then AntiRatchet was already run in block 238 and occlusion event data is logged pursuant to block 266 and OCC_STATUS is set to a value indicating a downstream occlusion (e.g. "DOWN_OCC") in accordance with block 268.

Figure 9D:
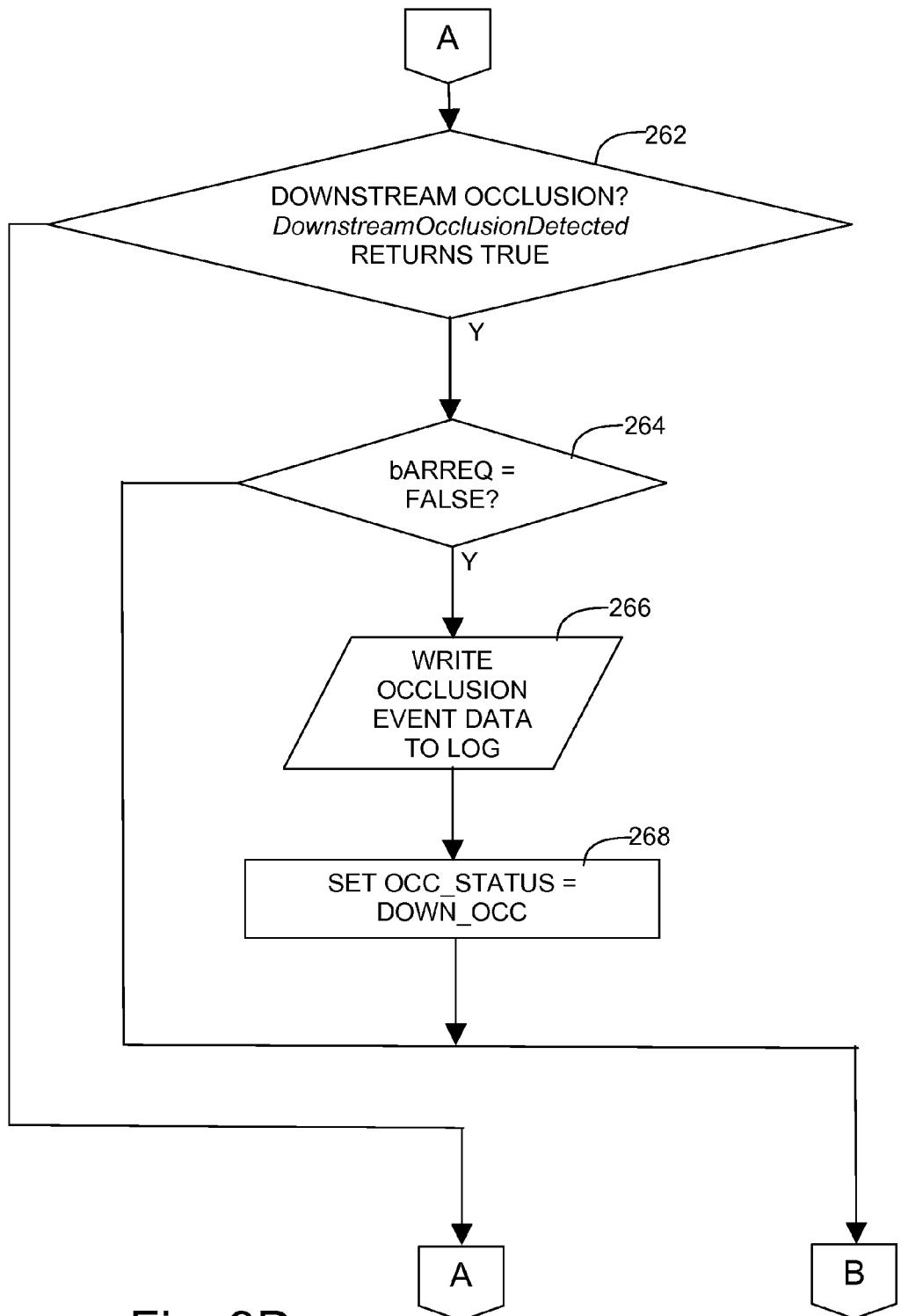
Figure 9E:
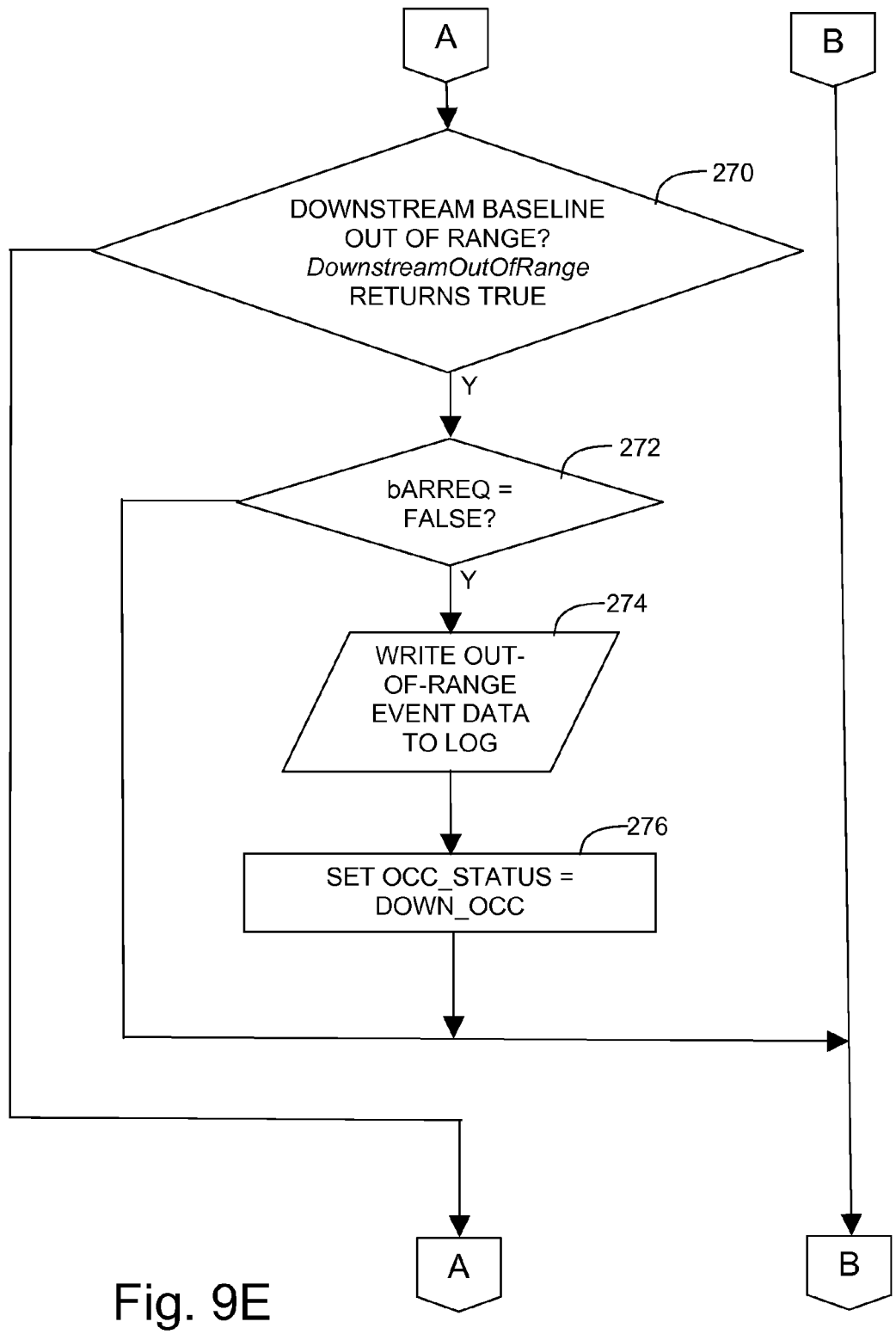

Decision block 270 in FIG. 9E determines if the downstream baseline is out of a predetermined range. Ranges for both the downstream and upstream baselines may be established and enforced with consideration given to the relevant sensor signal ranges and occlusion band thresholds. In the present example, a range requiring the downstream baseline to be less than 1950 mV safely allows for an additional 18 psi (+500 mV) of pressure to be detected within the sensor signal range of 2500 mV. Also by way of example, a range requiring the upstream baseline to be greater than 300 mV allows for a decrease in pressure of −5 psi (−300 mV) to be detected. Decision block 270 may call a Boolean routine DownstreamOutOfRange to check if the baseline is out of the predetermined range. If so, this condition is treated the same as a downstream occlusion as indicated by blocks 272-276, which substantially correspond to blocks 264-268 described above. The mentioned routine DownstreamOutOfRange is considered a simple routine for a skilled artisan to program, and is not described further herein.

Figure 9F:
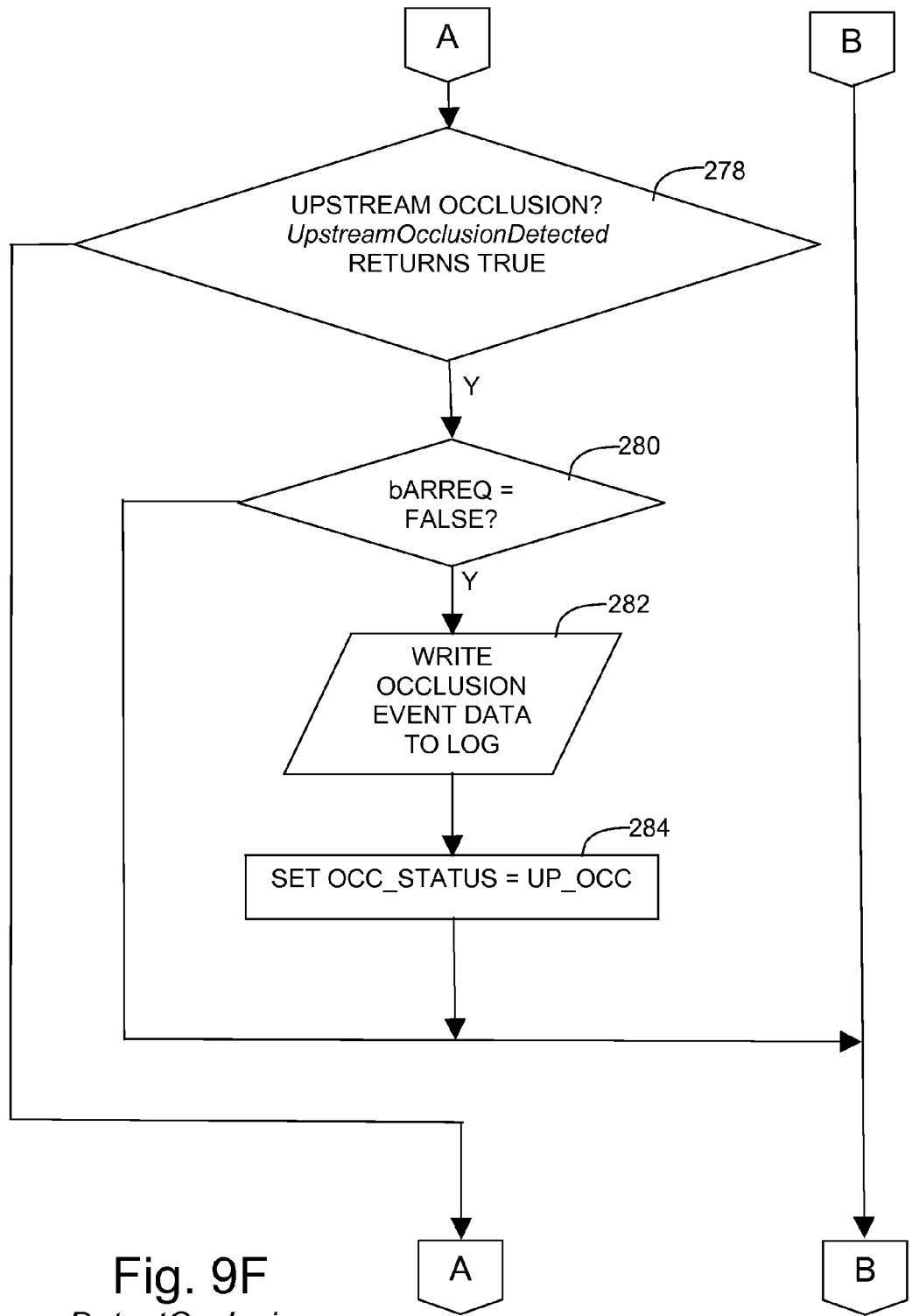
Figure 9G:
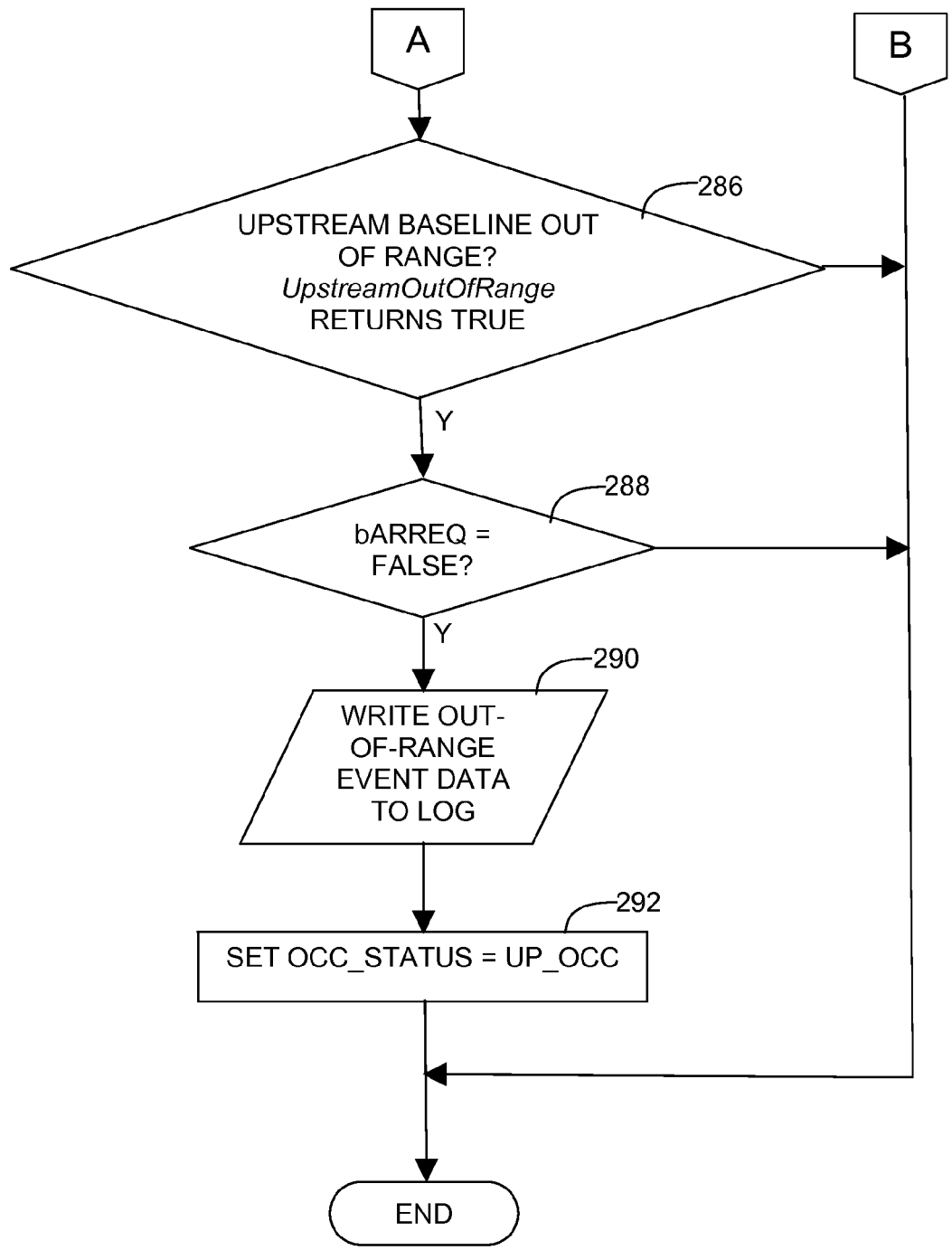
Figure 13A:
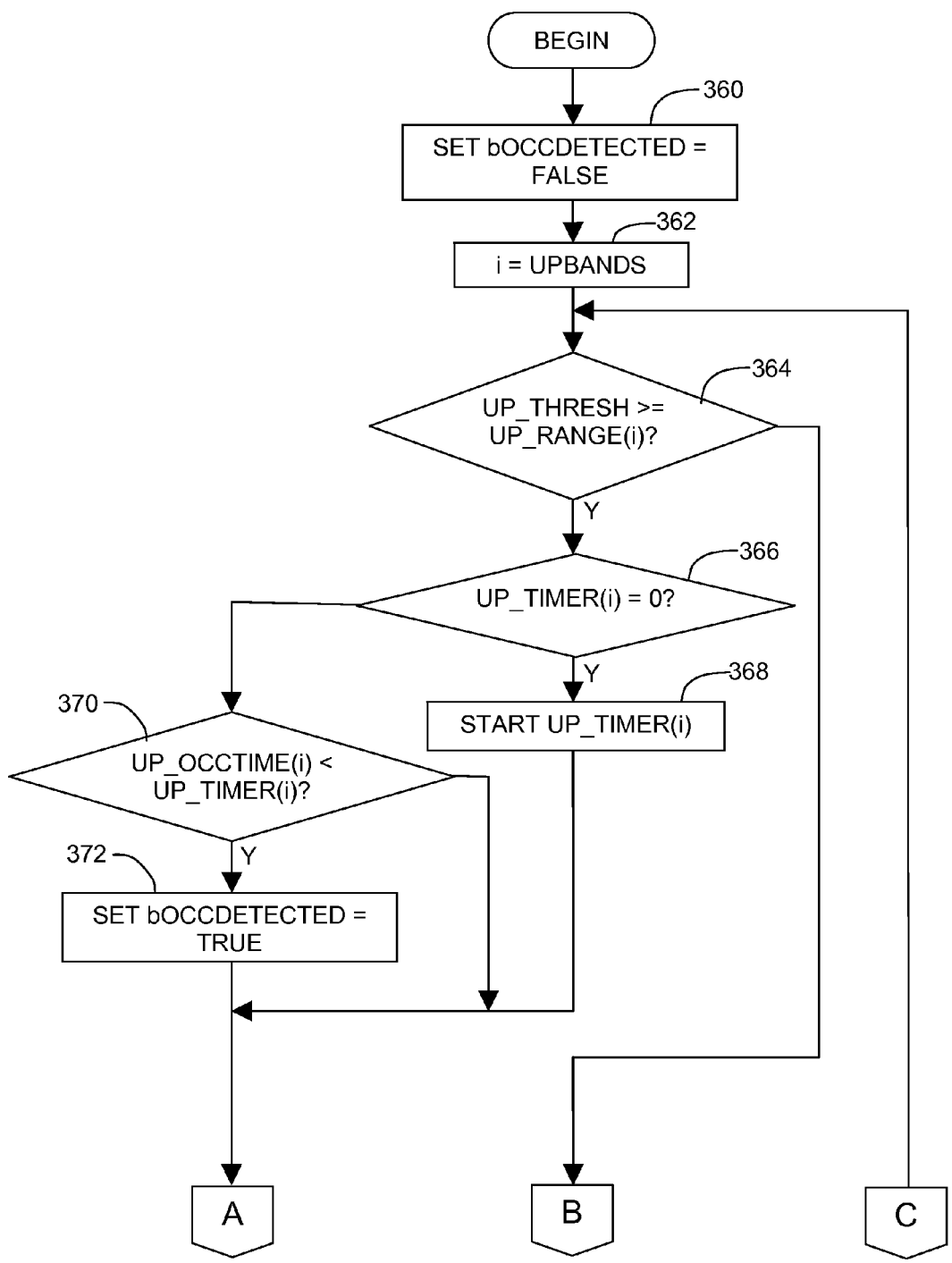
FIGS. 13A-13B are a flow diagram of an upstream occlusion detected routine called by the detect occlusion routine of FIGS. 9A-9G in accordance with an embodiment of the present invention.
Figure 13B:
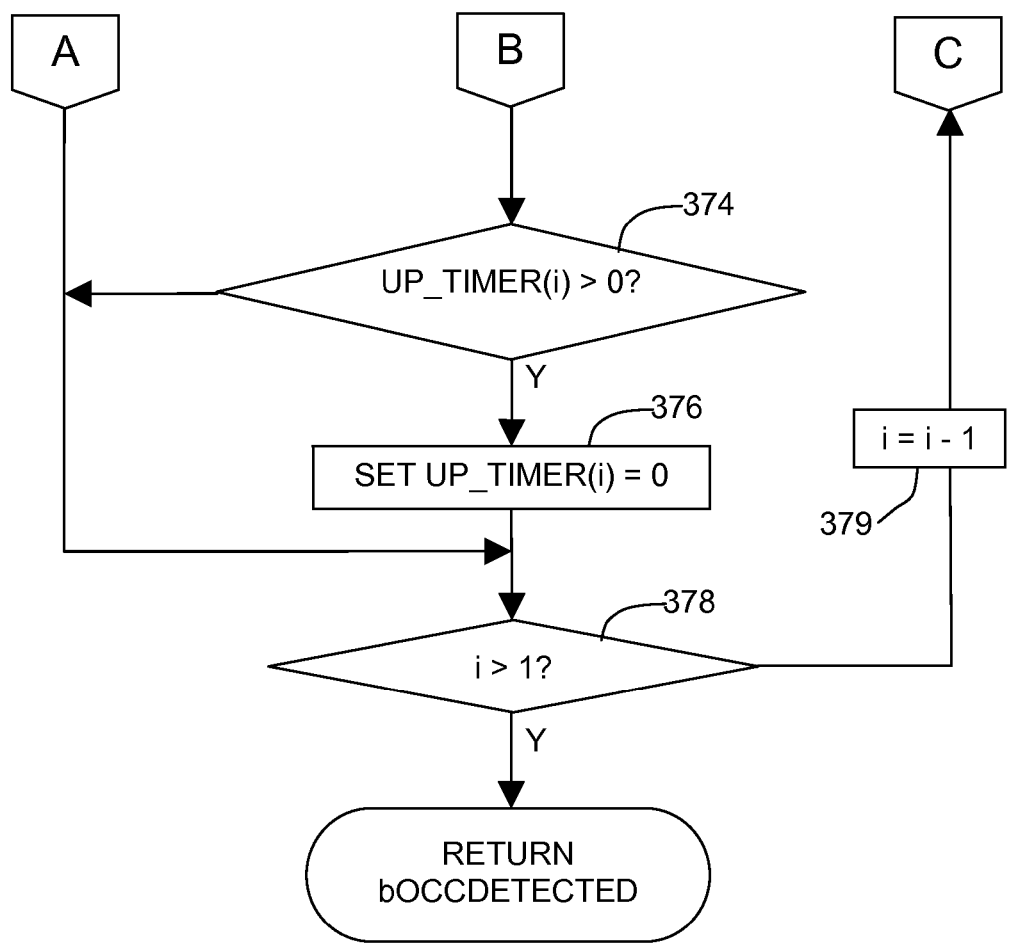

The downstream occlusion detection logic illustrated by FIGS. 9D-9E (blocks 262-276) is essentially repeated for upstream occlusion detection as may be understood from FIGS. 9F-9G (blocks 278-292). The UpstreamOcclusionDetected routine called by decision block 278 is depicted in FIGS. 13A-13B, and is largely similar to the DownstreamOcclusionDetected routine in FIGS. 12A-12B; consequently, detailed description of blocks 360-378 is omitted here. It should be noted that in the present example embodiment, only one upstream occlusion band is defined. More specifically, an upstream occlusion is detected if the upstream pressure reading drops at least 5 psi below the upstream sensor baseline and remains below this level for 1 second or more. Of course, more than one upstream occlusion band may be defined if desired.

Figure 14:
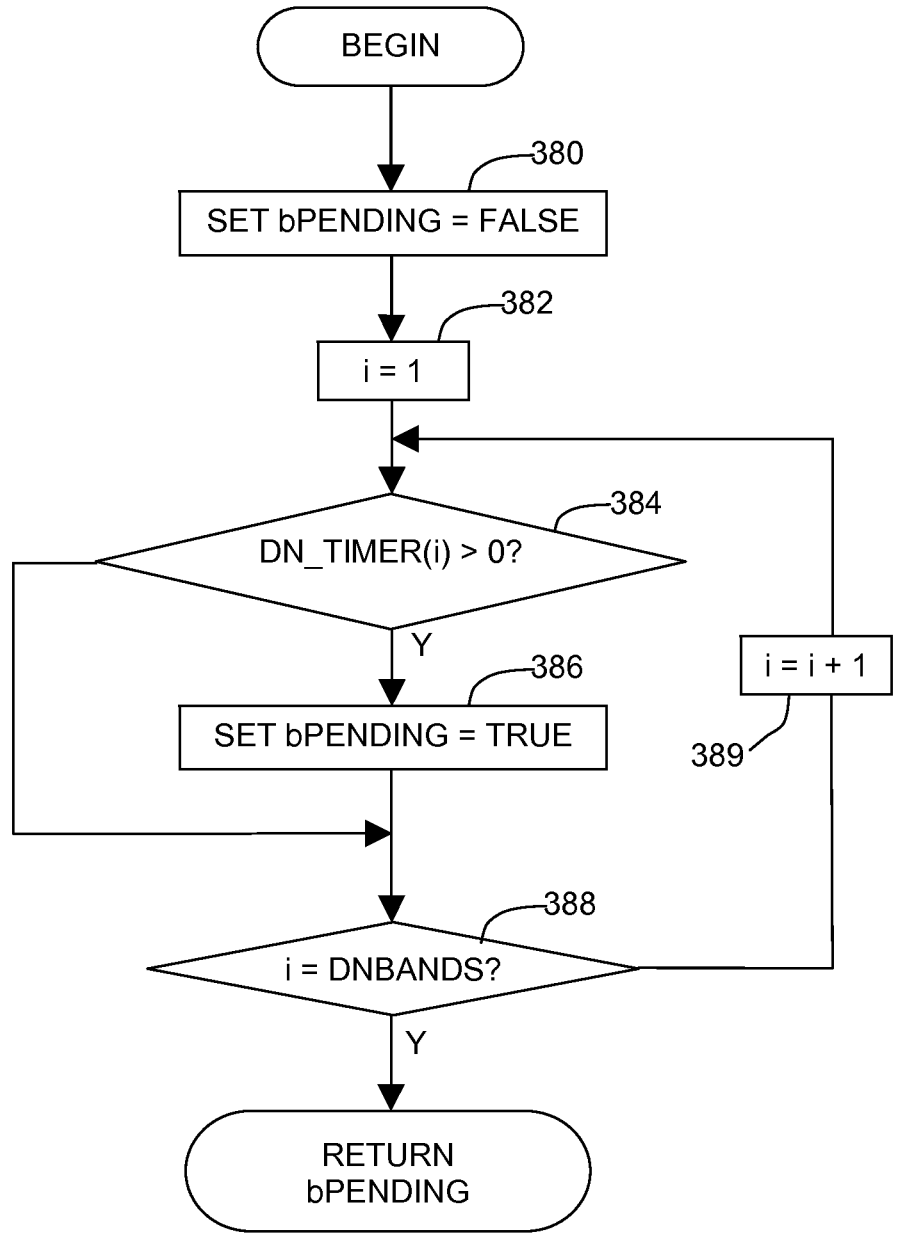
FIG. 14 is a flow diagram of an occlusion pending downstream routine called by the detect occlusion routine of FIGS. 9A-9G in accordance with an embodiment of the present invention.
Figure 15:
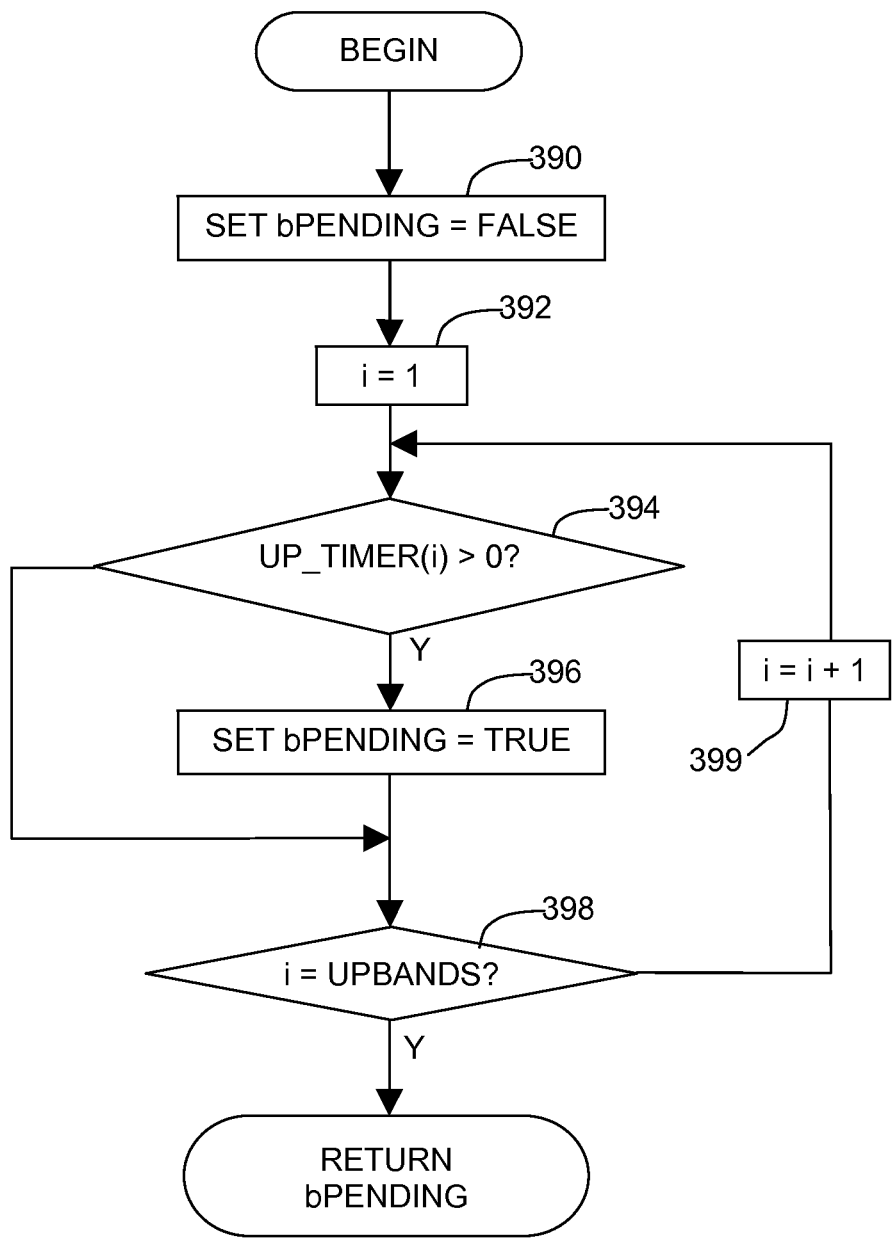
FIG. 15 is a flow diagram of an occlusion pending upstream routine called by the detect occlusion routine of FIGS. 9A-9G in accordance with an embodiment of the present invention.

As mentioned above, decision blocks 244 and 255 (see FIGS. 9B and 9C) make a determination based in part on whether an upstream occlusion or downstream occlusion is "pending". A pending occlusion refers to the situation where an the occlusion pressure threshold has been reached and the occlusion timer in at least one of the occlusion bands is counting toward the time period criterion for the band. For example, for the downstream occlusion band wherein line pressure must meet or exceed 15 psi for 30 seconds, a pending occlusion exists when the band timer is between 0 and 30 seconds. A routine OcclusionPendingDownstream for evaluating whether there is a pending downstream occlusion is shown in FIG. 14, and a similar routine OcclusionPendingUpstream for evaluating whether there is a pending upstream occlusion is shown in FIG. 15. Block 380 of OcclusionPendingDownstream sets a Boolean variable bPENDING to FALSE, and block 382 initializes index counter "i". Flow iterates through each occlusion band "i" by checking whether DN_TIMER(i) is greater than zero in decision block 384, and if so, setting bPENDING to TRUE in block 386. Decision block 388 determines if there is another occlusion band. If "i" equals the total number of downstream occlusion bands, then there are no more occlusion bands and the routine returns a value of bPENDING wherein TRUE indicates a pending downstream occlusion. If there is another band, index counter "i" is incremented in block 389 and flow loops back to decision block 384 to evaluate the next occlusion band. OcclusionPendingUpstream in FIG. 15 functions in a similar manner, with blocks 390-399 of OcclusionPendingUpstream being analogous to blocks 380-389 of OcclusionPendingDownstream. The routines shown in FIGS. 14 and 15 may be called by blocks 250 and 244, respectively, to determine occlusion pendency.

Figure 10A:
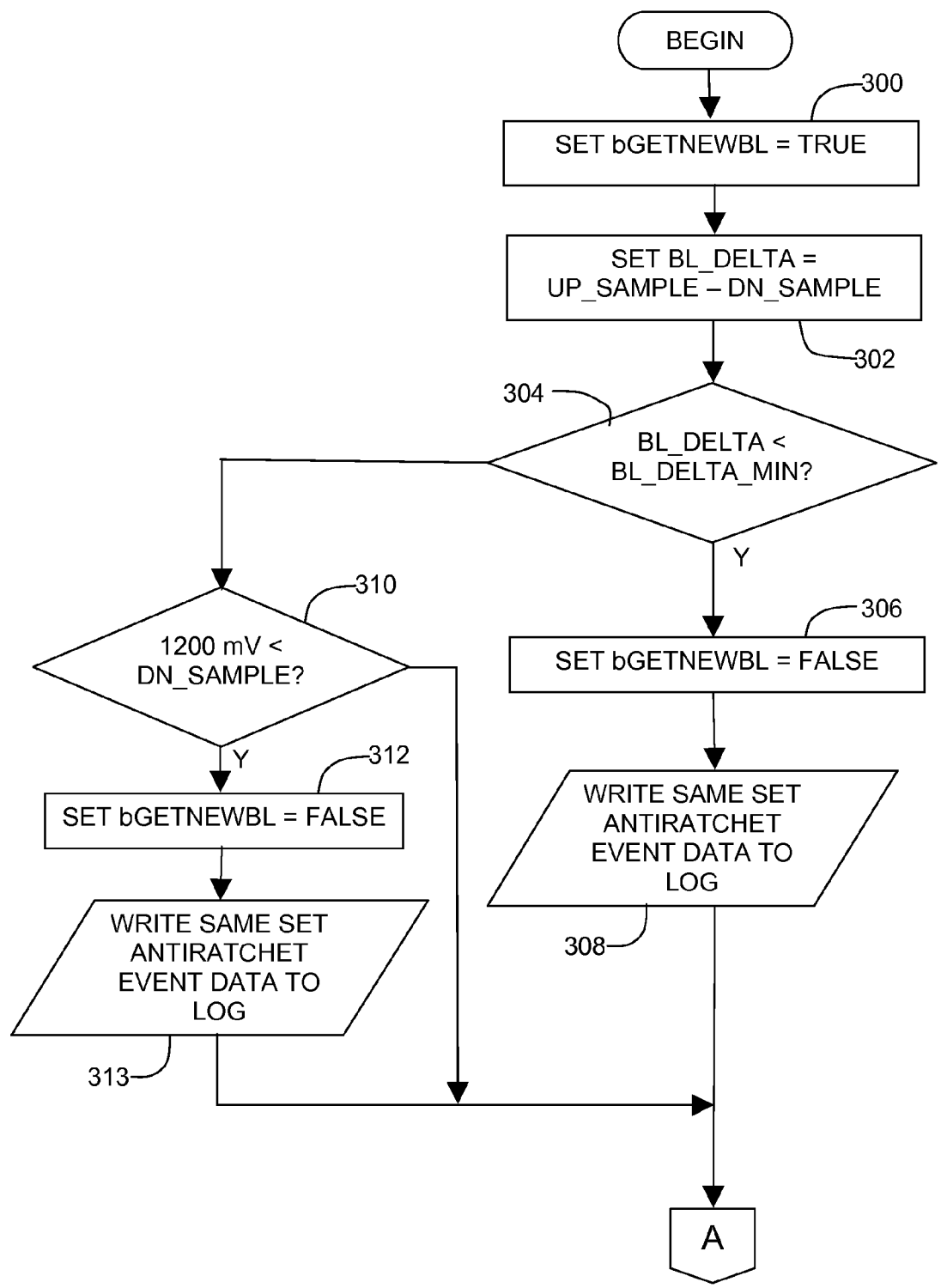
FIGS. 10A-10B are a flow diagram of an antiratchet routine called by the detect occlusion routine of FIGS. 9A-9G in accordance with an embodiment of the present invention.
Figure 10B:
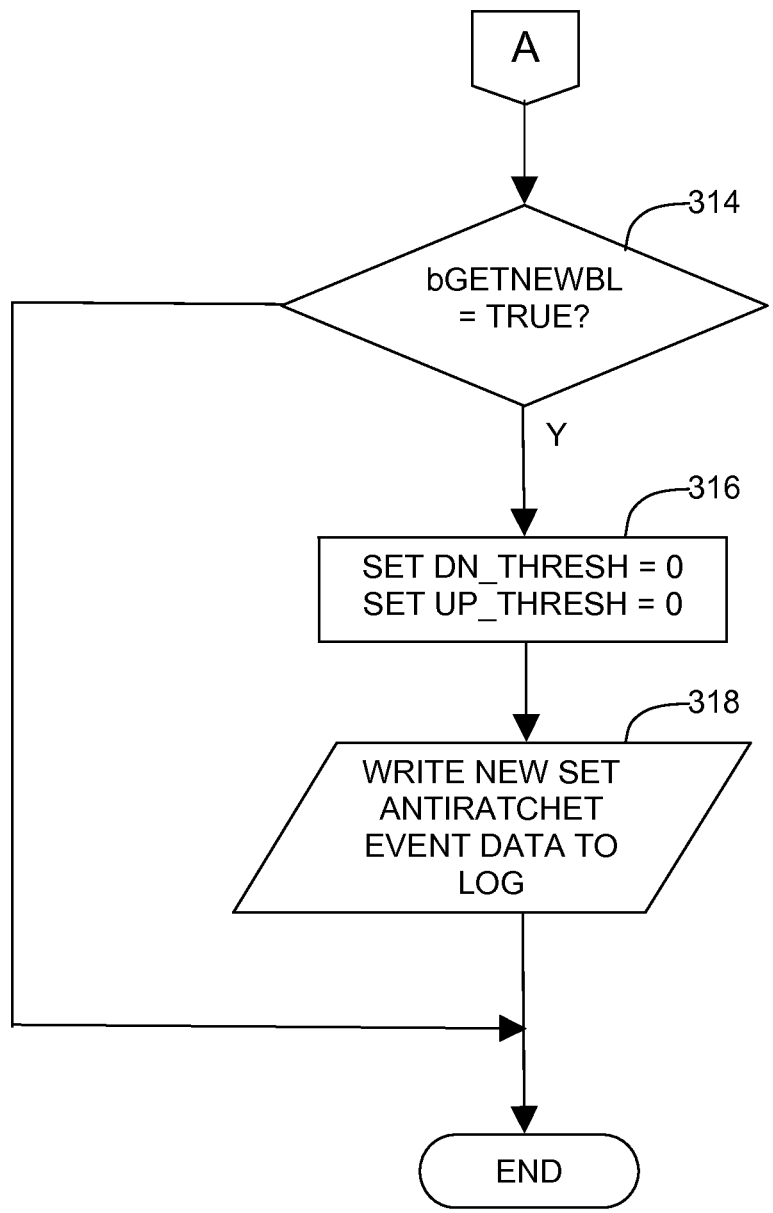

Reference is made once again to FIG. 9B, wherein a routine named AntiRatchet is called in block 238 of DetectOcclusion. Each time door 18 is opened and closed, there is a possibility that a new administration set has been installed, in which case new upstream and downstream baselines must be established. However, if door 18 is opened and closed but the administration set is not replaced, then it is important to keep the existing upstream and downstream baselines and not establish new baselines for tubing that is already pressurized due to a prior occlusion. The AntiRatchet routine, illustrated in FIGS. 10A-10B, provides logic for deciding whether to keep the existing sensor baselines or establish new baselines.

Block 300 of AntiRatchet sets a Boolean variable bGETNEWBL to TRUE. The value of bGETNEWBL will determine whether new upstream and downstream baselines are established; the initial TRUE setting represents a default assumption that a new administration set was installed and new baselines are needed. In accordance with the present invention, AntiRatchet tests this assumption by calculating the baseline delta value BL_DELTA that results when the current pressure sensor readings UP_SAMPLE and DN_SAMPLE are considered the new baseline values, and comparing BL_DELTA to the minimum baseline delta BL_DELTA_MIN computed by the OccBaselineDelta routine based on historical baseline data as explained above in connection with FIG. 11. The inventors recognized that a challenge to differentiating between a proper sensor baseline taken at equilibrium and an improper baseline taken for pressurized tubing is the fact that, due to administration set variability, baselines of different administration sets can vary widely. However, the inventors have observed that the baseline delta BL_DELTA remains relatively stable for a given infusion pump and does not vary significantly for different administration sets. For example, if a certain cassette is associated with a relatively high downstream baseline, the upstream baseline reading will also be relatively high. A different cassette might result in a vastly different downstream baseline level, but the upstream baseline will be affected in the same way, resulting in a similar baseline delta. In accordance with the present invention, the baseline delta BL_DELTA is used as a main factor to make an antiratcheting decision. Thus, BL_DELTA is set equal to UP_SAMPLE minus DN_SAMPLE in block 302, and decision block 304 checks whether this BL_DELTA is less than BL_DELTA_MIN.

As will be understood, a BL_DELTA calculated in block 302 for a pressurized administration set will be lower than an expected baseline delta for a new administration set at equilibrium (i.e., if the set has an upstream occlusion, UP_SAMPLE is decreased from an equilibrium reading; if the set has a downstream occlusion, DN_SAMPLE is increased from an equilibrium reading). Consequently, if BL_DELTA is less than BL_DELTA_MIN in decision block 304, then bGETNEWBL is changed to FALSE in block 306 to keep the current baselines. The antiratchet decision determining the same administration set remains installed may be written to a log in block 308.

If, however, decision block 304 finds BL_DELTA is not less than BL_DELTA_MIN, it is likely a new administration set was installed. The limits in downstream baseline variability allow another decision point for the antiratcheting logic: if the downstream sensor reading DN_SAMPLE is greater than a certain level, it always represents a pressurized signal, never a baseline equilibrium reading. In the present example embodiment, if DN_SAMPLE exceeds 1200 mV, it is assumed that the tubing is pressurized. Decision block 310 makes this determination. If DN_SAMPLE exceeds 1200 mV, then bGETNEWBL is changed to FALSE in block 312 to keep the current baselines, and the antiratchet decision determining the same administration set remains installed may be written to a log in block 313.

Blocks 314-318 appearing in FIG. 10B handle rebaselining based on the value of bGETNEWBL checked in decision block 314. If bGETNEWBL is TRUE, then new baselines are established by setting UP_THRESH and DN_THRESH equal to zero in block 316. The antiratchet event determining a new administration set was installed may be written to a log in block 318. If bGETNEWBL is FALSE, then blocks 316 and 318 are bypassed to keep the existing upstream and downstream baselines.

The present invention is embodied as both a method and a pump apparatus programmed to perform the method. An example embodiment of the occlusion detection method and pump apparatus of the present invention are described in detail herein, however those skilled in the art will realize that modifications may be made without straying from the spirit and scope of the invention as defined by the appended claims.

What is claimed is:

1. A method of detecting an occlusion in tubing connected to an infusion pump by a cassette removably received by the infusion pump, the infusion pump having a pumping mechanism operable to cause fluid flow through the tubing in an intended flow direction, a cassette access sensor providing a signal indicative of whether there is access to the cassette to allow removal of the cassette and installation of a new cassette, an upstream sensor at a location along the tubing upstream from the pumping mechanism in the flow direction, and a downstream sensor at a location along the tubing downstream from the pumping mechanism in the flow direction, wherein the upstream sensor and downstream sensor each provide a respective sensor signal indicative of a respective local fluid pressure in the tubing, the method comprising the steps of:
- establishing an upstream sensor signal baseline corresponding to fluid pressure equilibrium at the upstream sensor location and a downstream sensor signal baseline corresponding to fluid pressure equilibrium at the downstream sensor location;
- making an antiratchet decision in response to a signal from the cassette access sensor, the antiratchet decision determining whether or not occluded tubing was replaced;
- keeping the established upstream sensor signal baseline and the downstream sensor signal baseline when the antiratchet decision determines that occluded tubing was not replaced;
- establishing a new upstream sensor signal baseline and a new downstream sensor signal baseline when the antiratchet decision determines that occluded tubing was replaced;
- monitoring a difference between the upstream sensor signal and the upstream sensor baseline signal to detect an occlusion in the tubing upstream from the pumping mechanism; and
- monitoring a difference between the downstream sensor signal and the downstream sensor baseline signal to detect an occlusion in the tubing downstream from the pumping mechanism.

2. The method according to claim 1, wherein the step of making the antiratchet decision includes the substeps of calculating a baseline delta equal to a difference between the upstream sensor signal and the downstream sensor signal and comparing the baseline delta to a predetermined minimum baseline delta, wherein the antiratchet decision determines that occluded tubing was not replaced if the baseline delta is less than the minimum baseline delta.

3. The method of claim 1, wherein the step of making the antiratchet decision includes the substep of comparing the downstream sensor signal to a predetermined downstream signal limit, wherein the antiratchet decision determines that occluded tubing was not replaced if the downstream sensor signal is greater than the downstream signal limit.

4. The method according to claim 2, wherein the step of making the antiratchet decision further includes the substep of comparing the downstream sensor signal to a predetermined downstream signal limit, wherein the antiratchet decision determines that occluded tubing was not replaced if the downstream sensor signal is greater than the downstream signal limit.

5. The method according to claim 2, wherein the minimum baseline delta is determined based on historical baseline delta values stored by the infusion pump.

6. The method according to claim 1, further comprising the step of shifting the upstream sensor signal baseline in correspondence with decreases in the upstream sensor signal occurring while the pumping mechanism is not operating.

7. A method of making an antiratchet decision with respect to an infusion pump operatively connected to replaceable tubing by a replaceable cassette, the infusion pump having a pumping mechanism operable to cause fluid flow through the tubing in an intended flow direction, a cassette access sensor providing a signal indicative of whether there is access to the cassette to allow removal of the cassette and installation of a new cassette, an upstream sensor at a location along the tubing upstream from the pumping mechanism in the flow direction, and a downstream sensor at a location along the tubing downstream from the pumping mechanism in the flow direction, wherein the upstream sensor and downstream sensor each provide a respective sensor signal indicative of a respective local fluid pressure in the tubing, wherein the antiratchet decision determines whether or not occluded tubing was replaced, the method comprising the steps of:
- calculating a baseline delta equal to a difference between the upstream sensor signal corresponding to a condition of fluid pressure equilibrium at the upstream sensor location and the downstream sensor signal corresponding to a condition of fluid pressure equilibrium at the downstream sensor location and comparing the baseline delta to a predetermined minimum baseline delta, wherein the antiratchet decision determines that occluded tubing was not replaced if the baseline delta is less than the minimum baseline delta.

8. The method of claim 7, wherein the method of making the antiratchet decision further comprises the step of comparing the downstream sensor signal to a predetermined downstream signal limit, wherein the antiratchet decision determines that occluded tubing was not replaced if the downstream sensor signal is greater than the downstream signal limit.

9. The method according to claim 7, wherein the minimum baseline delta is determined based on historical baseline delta values stored by the infusion pump.

10. An infusion pump comprising:
- a housing including a cassette receptacle arranged to removably receive a cassette for connecting tubing to the pump;
- a pumping mechanism operable to cause fluid flow through the tubing in an intended flow direction;
- a cassette access sensor providing a signal indicative of whether there is access to the cassette to allow removal of the cassette and installation of a new cassette;
- an upstream sensor at a location along the tubing upstream from the pumping mechanism in the flow direction, and a downstream sensor at a location along the tubing downstream from the pumping mechanism in the flow direction, wherein the upstream sensor and downstream sensor each provide a respective sensor signal indicative of a respective local fluid pressure in the tubing;
- one or more memory modules configured to store an upstream sensor signal baseline corresponding to fluid pressure equilibrium at the upstream sensor location and a downstream sensor signal baseline corresponding to fluid pressure equilibrium at the downstream sensor location; and
- a microprocessor connected to the one or more memory modules, the pumping mechanism, the cassette access sensor, the upstream sensor and the downstream sensor;
- wherein the one or more memory modules is further configured to store instructions causing the microprocessor to make an antiratchet decision in response to a signal from the cassette access sensor, the antiratchet decision determining whether or not occluded tubing was replaced.

11. The infusion pump according to claim 10, wherein the one or more memory modules is further configured to store instructions causing the microprocessor to establish a new upstream sensor signal baseline and a new downstream sensor signal baseline when the antiratchet decision determines that occluded tubing was replaced.

12. A method of detecting an occlusion in tubing connected to an infusion pump, the infusion pump having a pumping mechanism operable to cause fluid flow through the tubing in an intended flow direction and an upstream sensor at a location along the tubing upstream from the pumping mechanism in the flow direction, wherein the upstream sensor provides a sensor signal indicative of a local fluid pressure in the tubing, the method comprising the steps of:

establishing an upstream sensor signal baseline corresponding to fluid pressure equilibrium at the upstream sensor location;

shifting the upstream sensor signal baseline in correspondence with decreases in the upstream sensor signal occurring while the pumping mechanism is not operating; and monitoring a difference between the upstream sensor signal and the upstream sensor baseline signal to detect an occlusion in the tubing upstream from the pumping mechanism.

13. An infusion pump comprising:

a pumping mechanism operable to cause fluid flow through tubing in an intended flow direction;

an upstream sensor at a location along the tubing upstream from the pumping mechanism in the flow direction, wherein the upstream sensor provides a sensor signal indicative of a local fluid pressure in the tubing;

one or more memory modules configured to store an upstream sensor signal baseline corresponding to fluid pressure equilibrium at the upstream sensor location; and a microprocessor connected to the one or more memory modules, the pumping mechanism, and the upstream sensor;

wherein the one or more memory modules is further configured to store instructions causing the microprocessor to shift the upstream sensor signal baseline in correspondence with decreases in the upstream sensor signal occurring while the pumping mechanism is not operating.

* * * * *